(12) United States Patent
Khan et al.

(10) Patent No.: US 7,115,666 B2
(45) Date of Patent: Oct. 3, 2006

(54) NITRONE COMPOUNDS, PHARMACEUTICAL COMPOSITIONS CONTAINING THE SAME AND METHODS FOR TREATING INFLAMMATION AND NEUROPATHIC PAIN

(75) Inventors: M. Amin Khan, Morgan Hill, CA (US); Ravindra B. Upasani, San Jose, CA (US); Paul L. Wood, Belmont, CA (US)

(73) Assignee: Renovis, Inc., So. San Francisco, CA (US)

( * ) Notice: Subject to any disclaimer, the term of this patent is extended or adjusted under 35 U.S.C. 154(b) by 184 days.

(21) Appl. No.: 10/684,810

(22) Filed: Oct. 14, 2003

(65) Prior Publication Data
US 2004/0142983 A1   Jul. 22, 2004

Related U.S. Application Data

(60) Provisional application No. 60/419,029, filed on Oct. 15, 2002.

(51) Int. Cl.
*A01N 33/02* (2006.01)

(52) U.S. Cl. ............... 514/638; 564/246; 564/265; 564/266

(58) Field of Classification Search ............ 564/248, 564/265, 266, 246; 514/638
See application file for complete search history.

(56) References Cited

U.S. PATENT DOCUMENTS 3,894,085 A * 7/1975 Eschenmoser ............ 564/248
5,476,867 A * 12/1995 Boyd et al. ............... 514/379
5,998,627 A * 12/1999 Theriot .................... 548/240

OTHER PUBLICATIONS

Beckett et al., Metabolism of Amphetamines. Identification of N-Oxygenated Products by Gas Chromatography and Mass Spectrometry, J. Pharm. Pharmac., 1973, 25, 708-717.*
Naito et al., The Dipolar 1,3-Cycloaddition of C,N-dialkylnitrone to Olefins with Hydroxyl Group and the Derivatives, Recueil des Travaux Chimiques des Pays-Bas, 1996, 115 (1), 13-19.*
Coates et al., Preparation of Vicinal N-Alkylamino Alcohols via Acylation-Rearrangement of Nitrones Followed by Hydride Reduction, J. Org. Chem. 1986, 51, 1383-1389.*

* cited by examiner

*Primary Examiner*—Johann Richter
*Assistant Examiner*—Chukwuma Nwaonicha
(74) *Attorney, Agent, or Firm*—Klauber & Jackson

(57) ABSTRACT

Disclosed are nitrone compounds and pharmaceutical compositions containing such compounds. The nitrone compounds have one to six additional carbons bridging between the nitrone functionality and the nitrone aryl ring. The disclosed compositions are useful as therapeutics for inflammation-related conditions and analgesia in mammals, such as arthritis, and for neuropathic pain and traumatic injuries such as traumatic brain injury and acute spinal cord injury.

62 Claims, 9 Drawing Sheets

Collagen Induced Arthritis in Female DA Rats
Compound 1 Decreases Total Gait Scores Which Indicate
This Structure Has Analgesic Activity in Arthritis

NITRONE COMPOUNDS, PHARMACEUTICAL COMPOSITIONS CONTAINING THE SAME AND METHODS FOR TREATING INFLAMMATION AND NEUROPATHIC PAIN

RELATED APPLICATION

The present application claims priority under 35 U.S.C. §119(e) from now abandoned Provisional application Ser. No. 60/419,029, filed Oct. 15, 2002, the disclosure of which is incorporated herein in its entirety.

BACKGROUND OF THE INVENTION

1. Field of the Invention

This invention relates to nitrone compounds and their use as therapeutic agents for the treatment of inflammation-related conditions and neuropathic pain in mammals, including humans.

2. State of the Art

Arthritis and related inflammatory disease conditions occur in more than 100 different forms, including rheumatoid arthritis (RA), osteoarthritis (OA), ankylosing spondylitis and systemic lupus erythematosus (SLE). Most forms of arthritis are characterized by some type of chronic inflammation. For example, RA typically involves chronic inflammation of the lining of the joints and/or the internal organs. Such chronic inflammation generally causes pain and swelling in the joints of those afflicted and may result in damage to cartilage, bone, tendons, ligaments and the like, ultimately leading to deformity and disability.

Neuropathic pain is a category of chronic pain that has been widely studied. Neuropathic pain occurs when the peripheral and/or central nervous systems are sensitized following an injury to the peripheral system. This initial injury can occur from a wide variety of causes including traumatic physical injury, as well as systemic diseases such as diabetes, herpes zoster, AIDS/HIV, syphilis and various other autoimmune diseases.

Examples of pain syndromes of this class include post herpetic neuralgia, neuritis, temporomandibular disorder, myofascial pain, back pain, and pain induced by inflammatory conditions. Neuropathic pain may occur in all body regions. For example, it may originate from the dental region. It may originate in regions which have suffered burn injury which often leads to neuropathic hyperalgesia in the affected body area. Neuropathic pain can also arise from neuralgia which in its acute phase involves intraneural inflammation which can cause damage to primary afferent axons, this inducing neuropathic pain. Neuropathic pain may also be induced by diabetic conditions (diabetic neuropathy). Neuropathy of primary afferent axons in long nerves is found in diabetic patients. Nociceptor sensitization may ensue.

Accordingly, a need exists for novel classes of therapeutic compounds which effectively treat arthritis and other inflammation-related conditions without producing undesired side effects. In addition, a need exists to treat the pain associated with joint disease such as arthritis, and a need exists to treat neuropathic pain which may present in the presence and absence of arthritis, as well as conditions such as traumatic brain injury and acute spinal cord injury.

SUMMARY OF THE INVENTION

The present invention accordingly concerns the use of compounds called "nitrones" to treat these conditions. In a first aspect, the present invention relates to the discovery and disclosure of a group of aryl substituted nitrone compounds that have at least one spacer or linker Z as defined herein, between the aryl group and the nitrone functionality, and that have demonstrated utility as therapeutic agents. More particularly, the nitrone compounds of the present invention are defined with Z comprising from about one to about six carbon atoms in length.

More generally, nitrones are compounds having a highly conjugated

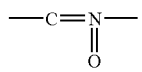

core structure.

Certain nitrones are known compounds. Phenyl-tert-butyl nitrone (PBN) is well known as a spin trapping agent. Its use as a pharmaceutical has also been proposed. Analogs of PBN having a range of aromatic ring substituents and an alkyl or aryl (with or without substitution) N-substituent have also been disclosed. These materials differ from the present nitrones in that the phenyl or other aryl ring is directly adjacent to the carbon of the characteristic

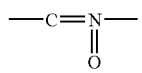

nitrone core structure.

Thus, one embodiment of the invention relates to a nitrone compound having at least a Ph-Z-C(R)=N(=O)— where Ph represents a substituted or unsubstituted aryl moiety, and Z is a saturated aliphatic carbon chain of one to six carbon atoms in length covalently bonded intermediate the aryl moiety and the nitrone carbon provided that:

when Z is —CH$_2$—CH$_2$—, R is H, and Ph is unsubstituted aryl, the N atom of the nitrone is not coupled to either t-butyl or methyl;

when Z is —CH$_2$—, R is H, Ph is substituted aryl with the substitutions selected from the group consisting of 4-N(CH$_3$)$_2$, 4-OCH$_3$, H, and 4-CH$_3$, the N atom of the nitrone is not coupled to methyl;

when Z is —CH$_2$—, R is H, Ph is substituted aryl with the substitutions selected from the group consisting of 3,5-di-t-butyl, 3,4-(OCH$_2$O)— and H, the N atom of the nitrone is not coupled to t-butyl;

when Z is —CH$_2$—, R is CH$_3$, and Ph is unsubstituted aryl, the N atom of the nitrone is not coupled to methyl or unsubstituted phenyl;

when Z is —CH$_2$—, R is H, and Ph is unsubstituted aryl, the N atom of the nitrone is not coupled to unsubstituted phenyl;

when Z is —CH(CH$_3$)—, R is H, and Ph is unsubstituted aryl, the N atom of the nitrone is not coupled to methyl, cyclohexyl or unsubstituted phenyl;

when Z is —CH(CH$_3$)—, R is H, and Ph is substituted aryl with the substitutions selected from the group consisting of 2,5-dimethoxy, and 2,5-dimethyl, the N atom of the nitrone is not coupled to cyclohexyl; and when Z is —CH$_2$—(CH$_2$)$_3$—, R is H, and Ph is unsubstituted aryl, the N atom of the nitrone is not coupled to cyclohexyl. More particularly, Z may be straight chain or branched chain alkylene, and for example, may comprise methylene, ethylene, n-propylene, n-butylene, or isopropylene.

In a further aspect of the invention, the nitrone compounds are defined with respect to a formula. Thus, the nitrone compounds may be defined by formula I

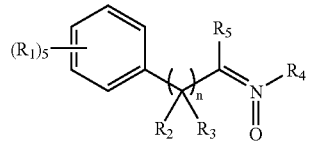

I wherein:
(i) n is an integer with a value ranging from one to six;
(ii) each R$_1$ is independently selected from:
hydrogen,
alkyl, alkenyl, alkynyl. cycloalkyl, cycloalkenyl, aryl, alkaryl, aralkyl, aralkenyl, aralkynyl,
halo, haloalkyl,
hydroxyl, alkoxyl, hydroxyalkyl, alkoxyalkoxyl, acyl, carboxylate, carboxyl, alkanoyloxy,
nitrate, nitrite, nitrile, cyanate, isocyanate, primary amino, secondary amino, tertiary amino, azido, carboxamido, acylamino,
thiol, sulfonyl, alkyl sulfonate, aryl sulfonate, sulfonamide, thioaryloxy, thioalkoxy,
oxygen heterocycles, nitogen heterocycles and sulfur heterocycles;
(iii) R$_2$, R$_3$, and R$_5$ are each independently selected from hydrogen, alkyl and cycloalkyl; and
(iv) R$_4$ is selected from alkyl, cycloalkyl, cycloalkylalkylene, cycloalkenyl, aryl and aralkyl, provided that:
a) when n is 1 or 2 and R$_4$ is tert-butyl or methyl, the R$_1$s, R$_2$, R$_3$, and R$_5$ are not all hydrogens;
b) when n is 1 and the R$_1$s are a 4-dimethylamino, 4-methyl or 4-methoxy and the rest hydrogens and R$_4$ is methyl, R$_2$, R$_3$, and R$_5$ are not all hydrogens;
c) when n is 1 and the R$_1$s are 3,5-di-tert-butyls and the rest hydrogens and R$_4$ is tert-butyl, R$_2$, R$_3$, and R$_5$ are not all hydrogens;
d) when n is 1 and R$_4$ is tert-butyl or phenyl, and R$_2$ is methyl, the R$_1$s, R$_3$, and R$_5$ are not all hydrogens;
e) when n is 1 and R$_4$ is methyl or phenyl, R$_5$ is methyl, the R$_1$s, R$_2$, and R$_3$ are not all hydrogens;
f) when n is 1 and R$_2$ and R$_4$ are both methyls, the R is, R$_3$, and R$_5$ are not all hydrogens;
g) when n is 1, R$_2$ is methyl and R$_4$ is cyclohexyl or phenyl, the R$_1$s, R$_3$, and R$_5$ are not all hydrogens;
h) when n is 1, R$_1$s are 2,5-dimethyl or 2,5-dimethoxy with the remainder hydrogen and R$_4$ is cyclohexyl, R$_3$ and R$_5$ are not all hydrogens; and
i) when n is 4 and R$_4$ is cyclohexyl the R$_1$s, R$_2$s, R$_3$s and R$_5$ are not all hydrogen.

In yet another embodiment, this invention is directed to a compound of formula I

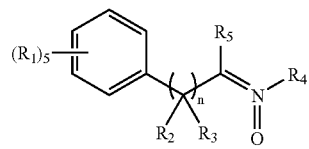

I wherein n is 1 and the

unit is a chiral center;

The above definitions of the nitrone compounds of the invention takes into account certain disclosures in the literature. The literature reveals a few nitrones of formula I and teaches their use as chemical intermediate and in other like non pharmaceutical applications. The materials are listed in terms of their relationship to formula I in the following Table I.

TABLE I

| n | R$_1$ | R$_2$ | R$_3$ | R$_4$ | R$_5$ |
|---|---|---|---|---|---|
| 2 | H | H | H | t-Bu | H |
| 2 | H | H | H | Me | H |
| 1 | 4-N(Me)2 | H | H | Me | H |
| 1 | 4-OMe | H | H | Me | H |
| 1 | 4-Me | H | H | Me | H |
| 1 | H | H | H | Me | H |
| 1 | 3,5-di-t-Bu | H | H | t-Bu | H |
| 1 | H | Me | H | t-Bu | H |
| 1 | H | H | H | t-Bu | H |
| 1 | H | H | H | Me | Me |
| 1 | H | Me | H | Me | H |
| 1 | H | H | H | Ph | H |
| 1 | H | Me | H | Ph | H |
| 1 | H | H | H | Ph | Me |
| 1 | H | Me | H | Cyclohexyl | H |
| 1 | 2,5-diMe | Me | H | Cyclohexyl | H |
| 1 | 2,5-diOMe | Me | H | Cyclohexyl | H |
| 4 | H | H | H | Cyclohexyl | H |
| 1 | 3,4-(OCH$_2$O)— | H | H | t-Bu | H |

The novel compounds thus defined above take into account and exclude the structures covered by Table I.

As stated earlier, an aspect of the present invention employs nitrone compounds as pharmaceutical agents. The nitrone compounds are broadly defined as having from one to six additional carbon atoms that may be in an alkylene bridge, between their nitrone core and their phenyl ring. These nitrones are useful as therapeutics for reducing inflammation and the pain associated with inflammation in mammals. In addition, these nitrone compounds are useful as therapeutics to treat neuropathic pain, and conditions such as traumatic brain injury and acute spinal cord injury. In particular, the nitrones of this invention are useful for treating arthritis, other inflammation-related conditions, and neuropathic pain.

Accordingly, in a further aspect, the invention includes pharmaceutical compositions which include a pharmaceutically acceptable carrier, and as an active ingredient, at least one nitrone compound, the nitrone compound comprising at least a Ph-Z-C=N(=O)— where Ph represents a substituted or unsubstituted aryl moiety, and Z is a saturated aliphatic carbon chain of one to six carbon atoms in length covalently bonded intermediate the aryl moiety and the nitrone carbon.

The pharmaceutical compositions of the invention may also be defined with respect to a formula, and thus may include a pharmaceutically acceptable carrier and one or more compounds of formula I:

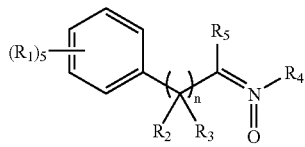

I as their active ingredients.

In formula I:
(i) n is an integer with a value ranging from one to six;
(ii) each $R_1$ is independently selected from:
hydrogen,
alkyl, alkenyl, alkynyl. cycloalkyl, cycloalkenyl, aryl, alkaryl, aralkyl, aralkenyl, aralkynyl,
halo, haloalkyl,
hydroxyl, alkoxyl, hydroxyalkyl, alkoxyalkoxyl, acyl, carboxylate, carboxyl, alkanoyloxy,
nitrate, nitrite, nitrile, cyanate, isocyanate, primary amino, secondary amino, tertiary amino, azido, carboxamido, acylamino,
thiol, sulfonyl, alkyl sulfonate, aryl sulfonate, sulfonamide, thioaryloxy, thioalkoxy,
oxygen heterocycles, nitrogen heterocycles and sulfur heterocycles;
(iii) $R_2$, $R_3$ and $R_5$ are each independently selected from hydrogen, alkyl and cycloalkyl; and
(iv) $R_4$ is selected from alkyl, cycloalkyl, cycloalkylalkylene, cycloalkenyl, aryl and aralkyl.

Accordingly, in another aspect, this invention is directed to a method for treating a mammal with an inflammation-related condition comprising administering to the mammal a pharmaceutical composition comprising a pharmaceutically acceptable carrier and an effective inflammation-reducing amount of at least one nitrone compound as defined herein.

In a particular embodiment of the invention, the conditions that are believed to be related to inflammation and that are treated in the above methods include rheumatoid arthritis; osteoarthritis; ankylosing spondylitis; systemic lupus erythematosus; psoriatic arthritis; neurodegenerative diseases that may involve, among other things, neuronal cell death, such as Alzheimer's disease, Parkinson's disease and Amyotrophic Lateral Sclerosis (ALS); and the like. In addition, the compounds of the invention are useful in the treatment of pain associated with arthritis as well as in the treatment of neuropathic pain, traumatic brain injury and acute spinal cord injury.

The methods of the invention accordingly extend to the treatment or prevention of neuropathic pain in a mammal, including humans, by administering an effective neuropathic pain treating or preventing dose of a pharmaceutical composition of the invention. Likewise, the invention includes the treatment of traumatic injury to the brain or spinal cord of a mammal by administering to the mammal an effective brain or spinal cord injury treating dose of the present pharmaceutical composition.

Other aspects of the invention, and associated objects and advantages will become apparent from a review of the ensuing description taken in conjunction with the following illustrative drawings.

DETAILED DESCRIPTION OF THE INVENTION

Figure 1:
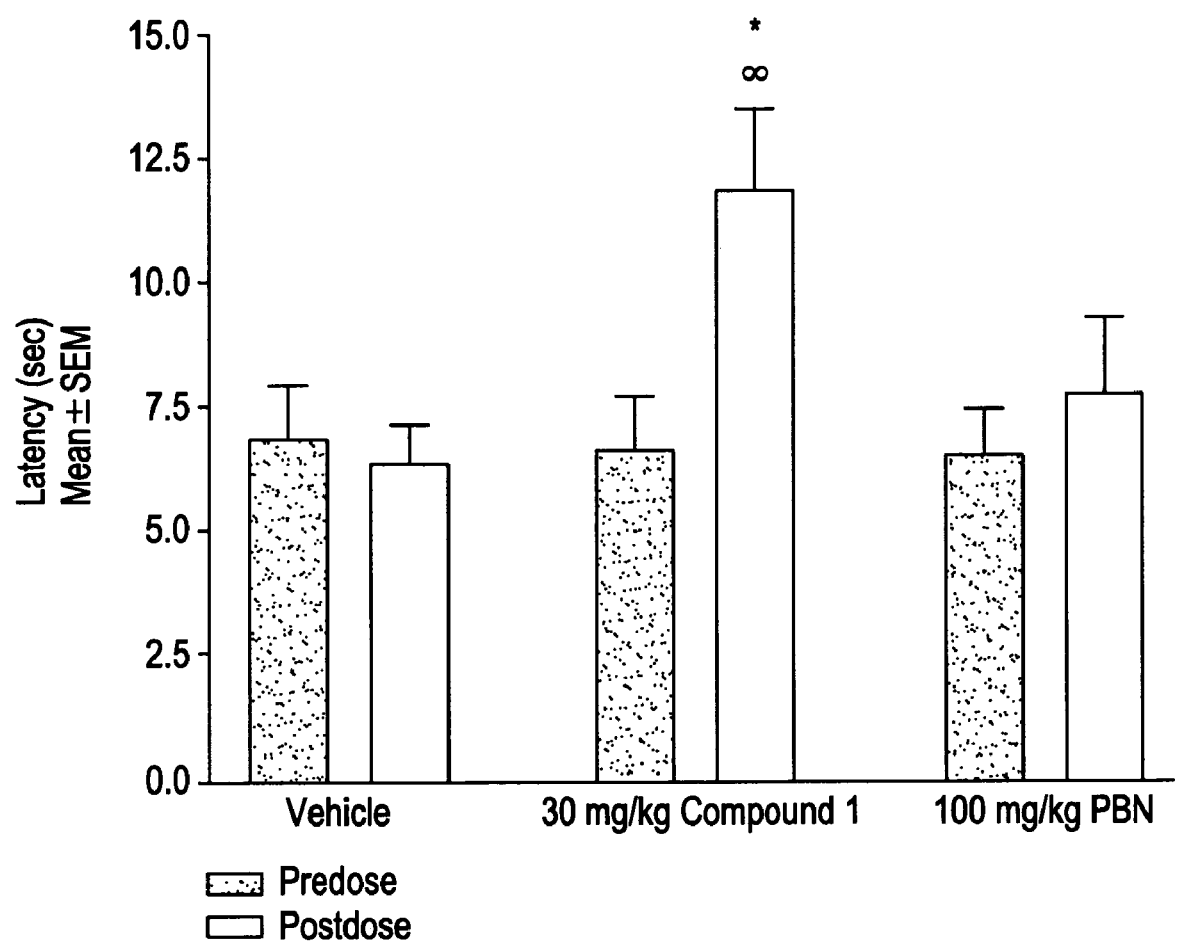
FIG. 1: A graph showing that treatment of CCI rats with Compound 1 increases latency in cold allodynia assay. Chronic Constriction Injury (CCI) rats exhibiting latency to cold stimulus were treated with vehicle, Compound 1 (30 mg/kg, p.o.) or PBN (100 mg/kg, p.o.). Animals were again tested 90 min post-dose. Pre-dose and post-dose average scores are shown. Significantly higher latency scores were recorded 90 minutes post-dose with 30 mg/kg treatment of Compound 1 (*$p<0.05$ vs. pre-dose score, Wilcoxon test). Kruskal-Wallis test indicated signficant post-dose latency score over vehicle (n=11), in animals treated with Compound 1 at 30 mg/kg ($p<0.05$ vs. vehicle post-dose, n=10, Dunn's test post hoc). Under identical conditions, in the same assay, N-tert-butyl phenyl nitrone (PBN) was completely inactive.

For the purposes of this invention, the nitrone compounds of the invention such as those set forth with respect to formula I, are named using conventional nitrone nomenclature, i.e., the carbon atom of the carbon-nitrogen double bond (C=N) is designated the C-position and substituents on the nitrogen atom of the carbon-nitrogen double bond are given the N-prefix.

In some cases, the nitrones of the invention may contain one or more chiral centers. Typically, such compounds will be prepared as a racemic mixture. If desired, however, such compounds can be prepared or isolated as pure stereoisomers, i.e., as individual enantiomers or diastereomers, or as stereoisomer-enriched mixtures. All such stereoisomers (and enriched mixtures) of the alkyl nitrones of formula I are included within the scope of this invention. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Additionally, all geometric isomers of the nitrone compounds of the invention are included within the scope of this invention including, for example, all isomers (i.e. E and Z isomers) of the carbon-nitrogen double bond of the nitrone functionality.

Definitions

When describing the nitrones, pharmaceutical compositions and methods of this invention, the following terms have the following meanings unless otherwise specified.

"Acyl" refers to the group —C(O)R where R is hydrogen, alkyl, alkenyl, aryl, aralkyl or cycloalkyl.

"Alkanoylamido" or "acylamino" refers to the group —NRC(O)R where each R is independently hydrogen, alkyl, alkenyl, aryl, aralkyl or cycloalkyl.

"Alkanoyloxy" or "acyloxy" refers to the group —OC(O)R where R is hydrogen, alkyl, alkenyl, aryl, aralkyl or cycloalkyl.

"Alkenyl" refers to a monovalent branched or unbranched unsaturated hydrocarbon group preferably having from 2 to 10 carbon atoms and more preferably 2 to 6 carbon atoms and having at least 1 and preferably from 1–2 sites of carbon-carbon double bond unsaturation. Preferred alkenyl groups include ethenyl (—CH=$CH_2$), n-propenyl (—$CH_2$CH=$CH_2$), isopropenyl (—C($CH_3$)=$CH_2$), and the like.

"Alkoxy" or "alkoxyl" refers to the group —OR where R is alkyl. Preferred alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkyl" refers to a monovalent branched or unbranched saturated hydrocarbon group preferably having from 1 to about 10 carbon atoms, more preferably from 1 to 8 carbon atoms and still more preferably 1 to 6 carbon atoms. This term is exemplified by groups such as methyl, ethyl, n-propyl, isopropyl, n-butyl, isobutyl, tert-butyl, n-hexyl, n-octyl, tert-octyl and the like. The term "lower alkyl" refers to an alkyl group having from 1 to 6 carbon atoms.

"Alkylene" refers to a divalent branched or unbranched saturated hydrocarbon group preferably having from 1 to 10 carbon atoms and when used to define the spacer between the aryl ring and the nitrone group from 1 to 6 carbon atoms. This term is exemplified by groups such as methylene (—$CH_2$—), ethylene (—$CH_2CH_2$—), the propylene isomers (e.g., —$CH_2CH_2CH_2$— and —CH($CH_3$)$CH_2$—) and the like.

"Alkynyl" refers to a monovalent branched or unbranched unsaturated hydrocarbon group preferably having from 2 to 10 carbon atoms and more preferably 2 to 6 carbon atoms and having at least 1 and preferably from 1–2 sites of carbon-carbon triple bond unsaturation. Preferred alkynyl groups include ethynyl, propargyl and the like.

"Amino" refers to the group —$NH_2$. "Substituted amino" refers to the group —N(R)$_2$ where up to one R is hydrogen and at least one R is independently selected from the group consisting of alkyl, alkenyl, alkynyl, aryl, cycloalkyl, and where both R groups are joined to form an alkylene group. When one R is non hydrogen this is a "secondary" amino, when both R's are non hydrogen this is a "tertiary" amino.

"Aminocarbonyl" or "carboxamido" refers to the group —C(O)NRR where each R is independently hydrogen, alkyl, aryl and cycloalkyl or where the R groups are joined to form an alkylene group.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

"Cycloalkyl" refers to a cyclic alkyl group of from 3 to 10 carbon atoms having a single cyclic ring or multiple condensed or bridged rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple or bridged ring structures such as adamantanyl and the like. The term "lower cycloalkyl" refers to a cycloalkyl group having from 3 to 6 carbon atoms.

"Cycloalkenyl" refers to a cyclic alkenyl group of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Halo" or "halogen" refers to fluoro, chloro, bromo and iodo. Preferred halo groups are either fluoro or chloro.

"Hydroxyl" refers to the group —OH.

"Nitrite" refers to the group —NO.

"Nitro" or "nitrate" refers to the group —$NO_2$.

"Thioalkoxy" refers to the group —SR where R is alkyl.

"Thioaryloxy" refers to the group —SR where R is aryl.

"Thiol" refers to the group —SH.

"Alkaryl" refers to an aryl group having one or more alkyl substituents.

"Aralkyl" refers to an alkyl group having an aryl substituent.

"Aralkenyl" refers to an alkenyl group having an aryl substituent.

"Aralkynyl" refers to an alkynyl group having an aryl substituent.

"Haloalkyl" refers to an alkyl group having one or more halo substituents.

"Hydroxyalkyl" refers to an alkyl group having one or more hydroxy substituents.

"Alkoxyalkoxyl" refers to a polyether group having two or more ether oxygens in an —O—R—O—R structure, where R may be alkyl or alkylene.

"Alkyl sulfonate" refers to the group —S(O)$_2$—R where R is alkyl, cycloalkyl or aralkyl.

"Aryl sulfonate" refers to the group —S(O)$_2$—R where R is aryl.

"Sulfonamide" refers to an amino group having one or both of its hydrogens replaced by alkyl sulfonate groups and/or aryl sulfonate groups.

"Sulfonyl" refers to the group —SO$_3$H.

"Isocyanate" refers to the group —NCO.

"Cyanate" refers to the group —OCN.

"Azido" refers to the group —N=N=N.

"Carbalkoxyl" or "carboxylate" refer to the group —C(O)OR where R is an alkyl.

"Carboxyl" refers to the group —CO$_2$H.

"Nitrile" refers to the group —C≡N.

"Pharmaceutically-acceptable salt" refers to any salt of a compound of this invention which retains its biological properties and which is not biologically or otherwise undesirable. Such salts may be derived from a variety of organic and inorganic counter-ions well known in the art and include, by way of example illustration, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like. The term "pharmaceutically-acceptable cation" refers to a pharmaceutically acceptable cationic counter-ion of an acidic functional group. Such cations are exemplified by sodium, potassium, calcium, magnesium, ammonium, tetraalkylammonium cations, and the like.

The Nitrones

A particular set of nitrone are those materials having either the structure Ph-Z-C(R)=N(=O)—, where Z is a saturated aliphatic carbon chain of from one to six carbon atoms, with particular values as to Z, R and Ph, or formula I in which the R$_1$ groups include hydrogens and from zero up to three nonhydrogens selected from alkyl, alkoxy, alkoxyalkoxyl, halo, hydroxy, amino, dialkylamino, acylamino, sulfonamide, sulfonyl, acyl, and aryl, both variants as defined with respect to the compounds of the invention, earlier herein.

With regard to formula I, a particular set of R$_1$ groups includes hydrogen, 2-hydroxy, 3-hydroxy, 4-hydroxy, 2-sulfonyl, 2,4-disulfonyl, 4-methyl, 4-iso-propyl, 3,5-dimethyl-4-hydroxy, 3,5-di-t-Bu-4-hydroxy, and 3,5-di-t-Bu-4-methoxymethoxy.

Particular nitrones also include compounds of formula I wherein n is 1–4. More particular nitrones include compounds wherein n is 2–4.

Preferred nitrones of this invention are materials of formula I in which n=1 and R$_2$, R$_3$ and R$_5$ are together all hydrogen or two hydrogens and one lower alkyl; and materials in which n=2 or 3 and R$_2$, R$_3$ and R$_5$ are all hydrogens and up to two lower alkyls. Particularly preferred among nitrones are those in which R$_1$ and R$_4$ are selected as shown in Table II.

TABLE II

| R$_1$ | R$_4$ |
| --- | --- |
| H | C(CH$_3$)$_3$ |
| 4-Me | C(CH$_3$)$_3$ |
| 4-iso-Pr | C(CH$_3$)$_3$ |
| 4-OH | C(CH$_3$)$_3$ |
| 4-OMe | C(CH$_3$)$_3$ |
| 4-OCH$_2$OMe | C(CH$_3$)$_3$ |
| 4-OEt | C(CH$_3$)$_3$ |
| 4-NMe$_2$ | C(CH$_3$)$_3$ |
| 4-NHAc | C(CH$_3$)$_3$ |
| 4-F | C(CH$_3$)$_3$ |
| 4-Cl | C(CH$_3$)$_3$ |
| 2-SO$_3$Na | C(CH$_3$)$_3$ |
| 2,4-di-SO$_3$Na | C(CH$_3$)$_3$ |
| 3,5-di-t-Bu-4-OH | C(CH$_3$)$_3$ |
| 3,5-di-t-Bu-4-OCH$_2$OMe | C(CH$_3$)$_3$ |
| 2-OH | C(CH$_3$)$_3$ |
| 2-OEt | C(CH$_3$)$_3$ |

Figure 9:
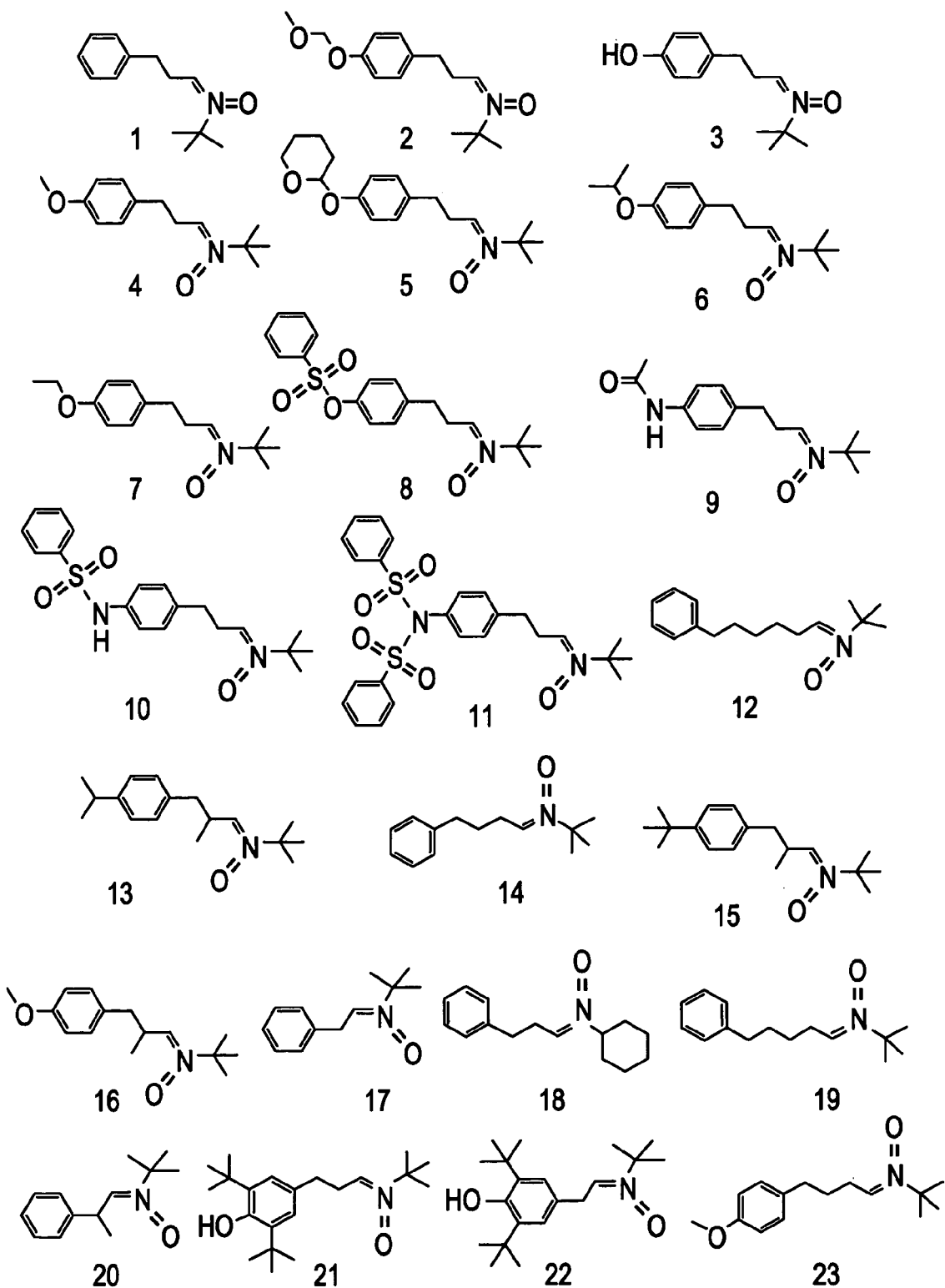
FIG. 9: A series of structural formula showing some of the compounds of the invention made in the Examples.

Accordingly, in another of its composition aspects, this invention is directed to each of the following individual compounds that are also shown in FIG. 9:

| | |
| --- | --- |
| Compound 1 | N-tert-butyl-C-(2-phenylethyl) nitrone |
| Compound 2 | N-tert-butyl-C-{2-[4-(methoxymethoxy)phenyl]ethyl} nitrone |
| Compound 3 | N-tert-butyl-C-[2-(4-hydroxyphenyl)ethyl] nitrone |
| Compound 4 | N-tert-butyl-C-[2-(4-methoxyphenyl)ethyl] nitrone |
| Compound 5 | N-tert-butyl-C-[4-(tetrahydropyran-2-yloxy) phenyl] nitrone |
| Compound 6 | N-tert-butyl-C-[2-(4-isopropoxyphenyl)ethyl] nitrone |
| Compound 7 | N-tert-butyl-C-[2-(4-ethoxyphenyl)ethyl] nitrone |
| Compound 8 | N-tert-butyl-C-[2-(4-benzenesulfonyloxy)phenyl]ethyl] nitrone |
| Compound 9 | N-tert-butyl-C-[2-(4-acetamidophenyl)ethyl] nitrone |
| Compound 10 | N-tert-butyl-C-[2-(4-benzenesulfonamidophenyl)ethyl] nitrone |
| Compound 11 | N-tert-butyl-C-[2-(4-N,N-Dibenzenesulfimidophenyl)ethyl] nitrone |
| Compound 12 | N-tert-butyl-C-(5-phenylpentyl) nitrone |
| Compound 13 | N-tert-butyl-C-[2-(4-isopropylphenyl)-1-methyethyl] nitrone |
| Compound 14 | N-tert-butyl-C-(4-phenylpropyl) nitrone |
| Compound 15 | N-tert-butyl-C-[1-(4-tert-butyl benzyl)-ethyl] nitrone |
| Compound 16 | N-tert-butyl-C-[1-methyl-2-(4-methoxyphenyl)ethyl] nitrone |
| Compound 17 | N-tert-butyl-C phenylmethyl nitrone |
| Compound 18 | N-cyclohexyl-C-(2-phenylethyl) nitrone |
| Compound 19 | N-tert-butyl-C-[4-phenylbutyl] nitrone |
| Compound 20 | N-tert-butyl-C-[1-(phenyl)ethyl] nitrone |
| Compound 21 | N-tert-butyl-C-[2-(3,5-di-tert-butyl-4-hydroxyphenyl)ethyl] nitrone |
| Compound 22 | N-tert-butyl-C-[2-(3,5-di-tert-butyl-4-hydroxyphenyl)methyl] nitrone |
| Compound 23 | N-tert-butyl-C-[4-methoxy-phenyl)propyl] nitrone, and pharmaceutically acceptable salts thereof. |

General Synthetic Procedures

The nitrones of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, N.Y., 1991, and references cited therein.

In a preferred method of synthesis, the nitrones of this invention are prepared by coupling a carbonyl compound of formula II:

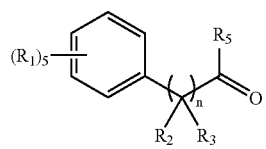

II wherein n, $R_1$, $R_2$, $R_3$ and $R_5$ are as defined above, with a hydroxylamine of formula III:

HO—NH—$R_4$   III wherein $R_4$ is as defined above. The hydroxylamine is usually present as an acid salt.

This coupling reaction is typically conducted by contacting the carbonyl compound II with at least one equivalent, preferably about 1.1 to about 2 equivalents, of hydroxylamine III in an inert polar solvent such as methanol, ethanol, 1,4-dioxane, tetrahydrofuran, dimethyl sulfoxide, dimethylformamide and the like. This reaction is preferably conducted at a temperature of from about 0° C. to about 100° C. for about 1 to about 48 hours. Optionally, a catalytic amount of an acid, such as hydrochloric acid, acetic acid, p-toluenesulfonic acid, silica gel and the like, may be employed in this reaction. When $R_1$ in formula II is —C(O)$R_3$, at least two equivalents of hydroxylamine III are employed in this coupling reaction. Upon completion of the reaction, the nitrone of formula I is recovered by conventional methods including precipitation, chromatographic separation, filtration, distillation, sublimation, and the like.

The hydroxylamine compounds of formula III are known compounds or compounds that can be prepared from known compounds by conventional procedures. Typically, the hydroxylamine compounds of formula III are prepared by reducing the corresponding nitro compound (i.e., $R_4$—$NO_2$, wherein $R_4$ is as defined above) using a suitable reducing agent such as activated zinc/acetic acid, activated zinc/ammonium chloride or an aluminum/mercury amalgam. This reaction is typically conducted at a temperature ranging from about 15° C. to about 100° C. for about 0.5 to 12 hours, preferably about 2 to 6 hours, in an aqueous reaction media, such as an alcohol/water mixture in the case of the zinc reagents or an ether/water mixture in the case of the aluminum amalgams. Aliphatic nitro compounds (in the form of their salts) can also be reduced to hydroxylamines using borane in tetrahydrofuran. Since some hydroxylamines have limited stability, such compounds are generally prepared immediately prior to reaction with the carbonyl compound of formula II.

Preferred hydroxylamines for use in this invention include, but are not limited to, N-isopropylhydroxylamine, N-n-propylhydroxylamine, N-n-butylhydroxylamine, N-tert-butylhydroxylamine, N-cyclohexylhydroxylamine and the like.

Pharmaceutical Compositions

When employed as pharmaceuticals, the nitrones of this invention are typically administered in the form of a pharmaceutical composition. Such compositions can be prepared using procedures well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by any suitable routes including, by way of illustration, oral, topical, rectal, transdermal, subcutaneous, intravenous, intramuscular, intranasal, and the like. Depending on the intended route of delivery, the compounds of this invention are preferably formulated as either oral, topical or injectable compositions.

Pharmaceutical compositions for oral administration can take the form of bulk liquid solutions or suspensions, or bulk powders. More commonly, however, such compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the nitrone compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Topical compositions are typically formulated as a topical ointment or cream containing the active ingredient(s), generally in an amount ranging from about 0.01 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example, an oil-in-water cream base. Such topical formulations are well-known in the art and generally include additional ingredients to enhance the dermal penetration or stability of the active ingredients or the formulation. All such known topical formulations and ingredients are included within the scope of this invention.

The compounds and compositions of this invention can also be administered by a transdermal device. Accordingly, topical administration can be accomplished using a patch either of the reservoir or porous membrane type or of a solid matrix variety. Likewise, the compounds and compositions may be prepared and formulated for pulmonary delivery and can be prepared in forms adapted for inhalation, in a manner well known in the art.

Injectable compositions are typically based upon injectable sterile saline or phosphate-buffered saline or other injectable carriers known in the art. As before, the alkyl nitrone compound in such compositions is typically a minor component, often being from about 0.05 to 2% by weight with the remainder being the injectable carrier and the like.

The above-described components for orally and topically administrable or injectable compositions are merely representative. Other materials as well as processing techniques and the like are set forth in Part 8 of *Remington's Pharmaceutical Sciences*, 18th edition, 1990, Mack Publishing Company, Easton, Pa., 18042, which is incorporated herein by reference.

The compounds of this invention can also be administered in sustained release forms or from sustained release drug delivery systems. A description of representative sustained release materials can be found in the incorporated materials in *Remington's Pharmaceutical Sciences*.

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240–270 mg tablets (80–90 mg of active nitrone compound per tablet) in a tablet press.

Formulation 2—Capsules

A compound of formula I is admixed as a dry powder with a starch diluent in an approximate 1:1 weight ratio. The mixture is filled into 250 mg capsules (125 mg of active intone compound per capsule).

Formulation 3—Liquid

A compound of formula I (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 ml.

Formulation 4—Injection

The compound of formula I is dissolved in a buffered sterile saline injectable aqueous medium to a concentration of approximately 5 mg/ml.

Formulation 5—Ointment

Stearyl alcohol (250 g) and white petrolatum (250 g) are melted at about 75° C. and then a mixture of a compound of formula I (50 g), methylparaben (0.25 g), propylparaben (0.15 g), sodium lauryl sulfate (10 g), and propylene glycol (120 g) dissolved in water (about 370 g) is added and the resulting mixture is stirred until it congeals.

Compound Utility

The compounds and pharmaceutical compositions of this invention find use as therapeutics for treating inflammation-related conditions, pain conditions including chronic pain syndrome, generalized pain syndrome, neuropathic pain and acute traumatic injuries such as acute injury to the central nervous system in mammals including humans.

The following more complete listing of pain conditions included within the definition of neuropathic pain may be found in PAIN MANAGEMENT, Rochelle Wagner and Robert R. Myers.

| Examples and Causes of Neuropathic Pain | |
|---|---|
| Peripheral nerve trauma | Spinal cord |
| Entrapment neuropathy | Trauma, transaction, hemisection, |
| Nerve transection, including surgery | Lissauer tract section |
| Causalgia | Syrinx |
| Amputation and stump pain | Mutiple sclerosis |
| Neuroma | Tumor compression |
| Post-choracotomy pain | Arteriovenous malformation |
| Other mononeuropathies | Dyscraphism |
| Diabetic | Vitamin B12 deficiency |
| Malignant nerve/plexus invasion | Hematomyelia |
| Plexus irradiation | Syphilitic myelitis |
| Ischemic irradiation | Commissural myelotomy |
| Connective tissue disease (rheumatoid arthritis, systemic lupus erythematosus, polyarteritis nodosa) | Brain stem Wallenberg's syndrome Multiple sclerosis Tuberculoma |
| Polyneuropathies | Tumor |
| Diabetic | Syrinx |
| Alcoholic | |
| Nutritional | Thalamus |
| Amyloid | Infarction |
| Fabry disease | Tumor |
| Chemical (e.g., anticancer therapies) | Surgical lesions in main |
| Idiopathic | sensory necleus |
| AIDS neuropathy | Hemorrahage |
| Root and dorsal root ganglion | Corrical/subcorrical |
| Prolapsed disk/compression | Infarction |
| Postherpetic or trigeminal neuralgia | Trauma |
| Arachnoiditis | Tumor |
| Root avulsion | Arteriovenous malformation |
| Tumor compression | |
| Surgical rhizotomy | |

Among the inflammation-related conditions which may be treated with the alkyl nitrone compounds and pharmaceutical compositions of this invention are various forms of arthritis, including but not limited to, rheumatoid arthritis, osteoarthritis, ankylosing spondylitis, systemic lupus erythematosus, psoriatic arthritis, and the like. Other inflammation-related conditions include, by way of illustration, inflammatory bowel disease (IBD), septic shock, erythema nodosum leprosy, septicemia, uveitis, adult respiratory distress syndrome (ARDS), organ rejection, neuro-inflammatory conditions, cardio-inflammatory conditions and the like. As mentioned earlier, certain conditions thought to be causally linked to inflammation include neurodegenerative diseases, having among their hallmarks, concomitant neural inflammation and neuronal cell death. Thus, such conditions as Alzheimers disease, Parkinson's disease and ALS are offered herein as representative non-limiting examples of such diseases.

For the treatment of long-term conditions, such as arthritis, the regimen for treatment may stretch over many months or years so oral dosing is preferred for patient convenience and tolerance. With oral dosing, one to five and especially two to four and typically three oral doses per day are representative regimens. Using these dosing patterns, each dose provides from about 0.1 to about 20 mg/kg of the nitrone, with preferred doses each providing from about 0.1 to about 10 mg/kg and especially about 1 to about 5 mg/kg.

The compounds of this invention can be administered as the sole active agent or they can be administered in combination with other active agents, such as cyclooxygenase inhibitors, 5-lipoxygenase inhibitors, non-steroidal antiinflammatory drugs (NSAIDs), steroids, peripheral analgesic agents such as zomepirac, diflunisol, and the like, and other active nitrone derivatives.

For the treatment of long-term conditions, such as chronic neuropathic pain, the regimen for treatment may stretch over many months or years so oral dosing is preferred for patient convenience and tolerance. With oral dosing, one to five and especially two to four and typically three oral doses per day are representative regimens. Using these dosing patterns, each dose provides from about 0.1 to about 20 mg/kg of the nitrone, with preferred doses each providing from about 0.1 to about 10 mg/kg and especially about 1 to about 5 mg/kg.

The nitrone compounds can be administered as the sole active agent or they can be administered in combination with other active analgesic agents, such as opioid analgesic agents.

The following synthetic and biological examples are offered to illustrate this invention and are not to be construed in any way as limiting the scope of this invention.

EXAMPLES

In the examples below, the following abbreviations have the following meanings. Abbreviations not defined below have their generally accepted meaning.

dec=decomposed
$dH_2O$=distilled water
ELISA=enzyme-linked immuno-sorbent assay
EtOAc=ethyl acetate
EtOH=ethanol
g=grams
h=hours
ip=intraperitoneal
L=liter
MAP kinases=mitogen-activating protein kinases
min=minutes
M=molar
MeOH=methanol
mg=milligram
ml=milliliter
mmol=millimole
m.p.=melting point
N=normal
po=per os, oral
q=quartet
quint.=quintet
s=singlet
t=triplet
THF=tetrahydrofuran
tlc=thin layer chromatography
μg=microgram
μL=microliter
UV=ultraviolet
rt=room temperature In the examples below, all temperatures are in degrees Celsius (unless otherwise indicated). Examples 1–23 describe the synthesis of various nitrones; and Examples I–V describe the testing of such compounds.

Example 1

N-tert-butyl-C-(2-phenylethyl)nitrone (Compound 1)

To a mixture of 3-phenylpropionaldehyde (10.0 g, 74.5 mmol, 1.0 equiv) and benzene (150 ml) was added chloroform (25 ml) until a clear solution was obtained. To the clear solution was added N-tert-butylhydroxylamine (7.31 g, 82.0 mmol, 1.1 (equiv) and the resulting mixture was refluxed under nitrogen and Dean-Stark trap for 22 h. Upon cooling oil separated. Oil was separated and product purified by flash chromatography (hexanes: EtOAc=1:1) to give N-tert-butyl-C-(2-phenylethyl)nitrone (7.31 g, 45.1%) as a light color oil: $^1$H NMR (CD$_3$OD) δ 7.30–7.27 (m, 2H, Ar—H), 7.23–7.19 (m, 3H, Ar—H), 6.80 (t, 1H, Ar—H), 2.77–2.62 (m, 4H, 2CH2), 1.46 (s, 9H, t-Bu).

Example 2

N-tert-butyl-C-{2-[4-(methoxymethoxy)phenyl]ethyl}nitrone (Compound 2)

a. 3-(4-Hydroxyphenyl)-1-propanol (Compound 2)

To a suspension of LiAlH$_4$ (8.37 g, 220.6 mmol, 1.5 equiv) in THF (300 ml) was added dropwise a solution of 3-(4-hydroxyphenyl)propionic acid (25.0 g, 150 mmol, 1 equiv) in THF (50 ml) at rt and mixture stirred at 60° C. for 2 h. The reaction mixture was acidified with 1 N HCl, diluted with water, and extracted with EtOAc. The combined extracts were washed with water, saturated aqueous NaHCO$_3$, brine and dried over MgSO$_4$ and concentrated under vacuum to give a 3-(4-hydroxyphenyl)-1-propanol as a white solid (15.95 g, 69.9%).

b. 3-[4-(methoxymethoxy)phenyl]-1-propanol

To a suspension of sodium hydride (0.70 g, 29.2 mmol, 1.1 equiv) in DMF (50 ml), was added drop wise, under nitrogen, a solution of 3-(4-hydroxyphenyl)-1-propanol (4.0 g, 26.3 mmol, 1.0 equiv) in DMF (150 ml) at rt, and the resulting mixture stirred for 15 min. Chloromethyl methyl ether (2.22 g, 26.3 mmol, 1.0 equiv) was added drop wise to the mixture and the mixture was stirred for 2 h at rt. The reaction mixture was diluted with water and extracted with EtOAc. The extract was washed with water, dried over MgSO$_4$, and concentrated under vacuum. The residue was purified by flash chromatography (hexanes:EtOAc=2:1) to give 3-[4-(methoxymethoxy phenyl]-1-propanol (3.66 g, 70.9%) as a colorless oil: $^1$H NMR (CD$_3$OD) δ 7.12 (d, 2H), 6.95 (d, 2H), 5.15 (s, 2H), 3.67 (t, 2H), 3.47 (s, 3H), 2.66 (t, 2H), 1.86 (q, 2H).

c. 3-[4-(Methoxymethoxy)phenyl]-1-propional

A solution of 3-(4-hydroxyphenyl)-1-propanol (3.66 g, 18.0 mmol, 1.0 equiv) in CH$_2$Cl$_2$ (50 ml) was added to a mixture of pyridinium chlorochromate (6.03 g, 28.0 mmol, 1.5 equiv) in CH$_2$Cl$_2$ (100 ml) at rt, and the mixture was stirred for 3.5 h. The reaction mixture was diluted with hexane (150 ml) and filtered through silica gel (60 g). The silica gel was eluted with mixture of hexane and EtOAc (1:1, 200 ml). The combined filtrate was then concentrated under vacuum. The residue was purified by column chromatography (hexane:EtOAc=2:1) to give 3-[4-(methoxymethoxy)phenyl]propional (3.22 g, 89.2%) as a colorless oil: $^1$H NMR (CD$_3$OD) δ 9.81 (t, 1H), 7.11 (d, 2H), 6.95 (d, 2H), 5.15 (s, 2H), 3.47 (s, 3H), 2.94–2.88(m, 2H), 2.78–2.72 (m, 2H).

d. N-tert-butyl-C-{2-[4-(methoxymethoxy)phenyl]ethyl}nitrone

To a mixture of 3-[4-(methoxymethoxy)phenyl]propional (1.62 g, 8.34 mmol, 1.0 equiv) and methanol (50 ml) was added N-tert-butylhydroxylamine (0.93 g, 10.43 mmol, 1.25 equiv) followed by 10 drops of conc. HCl. The mixture was stirred at rt for 18 h. The mixture was then concentrated under vacuum to yield a light colored oil. The residue oil was purified by column chromatography (hexane:EtOAc=1:1) followed by EtOAc to give the title compound (0.87 g, 39.4%) as a lightly colored oil: $^1$H NMR (CDCl$_3$) δ 7.12 (d, 2H), 6.94 (d, 2H), 6.80 (t, 1H), 5.60 (s, 2H), 3.48 (s, 3H), 2.81–2.79 (m, 4H), 1.46 (s, 9H).

Example 3

N-tert-butyl-C-[2-(4-hydroxyphenyl]ethyl nitrone
(Compound 3)

a. 3-(4-hydroxyphenyl)-1-propional.

To a mixture of (methoxymethoxy)phenyl]-1-propional (1.60 g, 8.24 mmol, 1.0 equiv) and THF (50 ml) was added 12 M HCl (6.8 ml), following which the mixture stirred at rt. for 2 h. Water (50 ml) was added to the mixture and the mixture was extracted with EtOAc. The organic layer was washed with water, NaHCO$_3$, brine, dried over MgSO$_4$, and concentrated to give 3-(4-hydroxyphenl)-1-propional as an oil (0.92 g, 74.2%).

b. N-tert-butyl-C-[2-(4-hydroxyphenyl]nitrone

To a mixture of 3-(4-hydroxyphenyl)-1-propional (1.02 g, 6.60 mml, 1.0 equiv) and methanol (50 ml) was added N-tert-butylhydroxylamine (0.71 g, 7.26 mmol, 1.1 equiv) and conc. HCl (5 drops). The mixture was then stirred at rt for 15 h and then refluxed for 19 h. Concentration under vacuum gave a mixture of solid and oil which was purified by flash chromatography (hexane:EtOAc=1:1) then with EtOAc to give a white solid m.p. 143.5° C.: $^1$H NMR (CD$_3$OD) δ 7.20 (t, J=5.32, 1H), 7.03 (d, J=8.66, 2H), 6.69 (d, J=8.66, 2H), 2.79–2.69 (m, 4H), 1.43 (s, 9H).

Example 4

N-tert-butyl-C-[2-(4-methoxyphenyl)ethyl]nitrone
(Compound 4)

To a solution of 3-(4-methoxyphenyl)-1-propional (10.00 g, 60.9 mmol, 1.0 equiv) and methanol (150 ml) was added N-tert-butylhydroxylamine (6.51 g, 73.0 mmol, 1.2 equiv) and the resulting mixture was refluxed under nitrogen for 6 h. The reaction mixture was concentrated under vacuum to give an oil which was purified by flash chromatography (hexane:EtOAc=1:1) to give N-tert-butyl-C-[2-(4-methoxyphenyl)ethyl]nitrone (7.13 g, 49.8%) as a brown oil. $^1$H NMR (CDCl$_3$) δ 7.13 (d, 2H), 6.86–6.77 (m, 3H), 3.79(s, 3H), 2.82–2.79 (m, 4H), 1.46 (s, 9H).

Example 5

N-tert-butyl-C-[4-(tetrahydropyran-2-yloxy)phenyl]
ethyl nitrone (Compound 5)

a. 3-[4-(tetrahydropyran-2-yloxy)phenyl]-1-propional.

To a solution of 3-(4-hydroxyphenyl)-1-propional (1.70 g, 11.3 mmol, 1.0 equiv) and CH$_2$Cl$_2$ (30.0 ml) was added pyridinium-p-toluenesulfonate (63.2 mg, 0.25 mmol). While stirring vigorously, a solution of 3,4-dihydro-2H-pyran (3.1 ml) in CH$_2$Cl$_2$ (20 ml) was added drop wise and the mixture was stirred at rt for 1.5 h. The mixture was then washed with brine, dried over MgSO$_4$ and concentrated under vacuum to give a light color oil (2.5 g, 97.0%). $^1$H NMR (CDCl$_3$) δ 9.81(t, 1H), 7.12–7.08 (d, 2H), 6.99–6.96 (d, 2H), 5.38 (t, 1H), 4.07–3.86 (m, 1H), 3.61–3.56 (m, 2H), 2.93–2.88 (m, 2H), 2.77–2.74 (m, 2H), 2.00–1.85 (m, 4H), 1.67–1.60 (m, 5H).

b. N-tert-butyl-C-[4-(tetrahydropyran-2-yloxy)phenyl]ethyl nitrone

To a mixture of 3-[4-(tetrahydropyran-2-yloxy)phenyl]-1-propional (2.50 g, 11.1 mmol, 1.0 equiv) in methanol (50 ml) was added N-tert-butylhydroxylamine (1.13 g, 12.7 mmol, 1.1 equiv) and the mixture was then stirred at rt for 18 h. The mixture was concentrated under vacuum to give the title nitrone (0.760 g, 22.42%) as a white solid, m.p. 68–70° C. $^1$H NMR (CDCl$_3$) δ 7.10 (d, 2H), 6.98 (d, 2H), 6.79 (t, 1H), 5.38(t, 1H), 3.92–3.88 (m, 1H), 3.62–3.58 (m, 1H), 2.82–2.74 (m, 4H), 1.88–1.62 (m, 7H), 1.46 (s, 9H).

Example 6

N-tert-butyl-C-[2-(4-isopropoxyphenyl)ethyl]nitrone
(Compound 6)

a. 3-[4-(2-Isopropoxy)phenyl]-1-propanol

To a solution of 3-(4-hydroxyphenyl)-1-propanol (3.00 g, 18.8 mmol, 1 equiv) in DMF (100 ml) was added, portion wise, NaH (0.45 g, 18.8 mmol, 1 equiv) at rt, and the resulting mixture was stirred for 15 min. 2-Iodopropane (1.88 ml, 18.8 mmol, 1 equiv) was added drop wise to the mixture at rt, and mixture was stirred for 2.5 h. The reaction mixture was then diluted with water and extracted with EtOAc. The extract was washed with water, dried over MgSO$_4$, and concentrated under vacuum. The residue was purified by column chromatography (hexane:EtOAc=2:1) to give 3-[4-(2-isopropoxy)phenyl]-1-propanol (1.52 g, 41.6%). $^1$H NMR (CDCl$_3$) δ 6.80 (d, J=8.6, 2H), 4.53–4.46 (m,1H), 3.69–3.65 (t, J=6.4, 2H), 2.67–2.61(t, J=6.7, 2H), 1.33 (s, 3H) 1.31(s, 3H).

b. 3-[4-(2-Propoxy)phenyl]-1-propional

A solution of 3-[4-propoxy)phenyl]-1-propanol (1.52 g, 7.8 mmol, 1.0 equiv) in (10 ml) was added to a mixture of pyridinium chlorochromate (2.53 g, 11.7 mmol, 1.5 equiv) in CH$_2$Cl$_2$ (100 ml) at rt and the mixture was stirred for 3.5 h. The reaction mixture was diluted with hexane (100 ml) and filtered through silica gel (20 g). The silica gel was eluted with a mixture of hexane and EtOAc (1:1). The combined filtrate was concentrated under vacuum to give the title compound (1.38 g, 92.0%) as a light yellow oil. $^1$H NMR (CDCl$_3$) δ 9.81(t, 1H), 7.08 (d, 2H), 6.81(d, 2H), 4.55–4.46 (m, 1H), 2.92–2.87 (m, 2H), 2.77–2.71(m, 2H), 1.33 (s, 3H), 1.31(s, 3H).

c. N-tert-butyl-C-[2-(4-propoxyphenyl)ethyl]nitrone

To a solution of 3-[4-(2-propoxy)phenyl-1-propional (1.38 g, 7.2 mmol, 1.0 equiv) in methanol (50 ml) was added N-tert-butylhydroxylamine (0.77 g, 8.6 mmol, 1.2 equiv) and 3 drops of conc. HCl and mixture refluxed for 17 h. The mixture was concentrated under vacuum to give the title nitrone (1.70 g, 89.5%) as a light yellow solid. m.p. 71–72° C. $^1$H NMR (DMSOd$_6$) δ 6.81 (d, 2H), 4.59–4.50 (q, 1H), 2.71–2.68 (m, 2H), 2.56–2.50 (m, 2H), 1.34 (s, 9H), 1.24–1.21(2s, 6H).

Example 7

N-tert-butyl-C-[2-(4-ethoxyphenyl)ethyl]nitrone (Compound 7)

a. 3-(4-Ethoxyphenyl)-1-propanol

To a solution of 3-(4-hydroxyphenyl)-1-propanol (3.00 g, 19.7 mmol, 1 equiv) in DMF (100 ml) was added portion wise NaH (0.45 g, 18.8 mmol, 0.95 equiv) at rt, and the resulting mixture was stirred for 15 min. Iodoethane (1.37 ml, 20.0 mmol, 1 equiv) was added drop wise and the mixture was stirred for 2.5 h. The reaction mixture was diluted with water and extracted with EtOAc. The extract was washed with water, dried over $MgSO_4$, and concentrated under vacuum to give the title compound (2.90 g, 81.7%) that was used as such for the next step.

b. 3-(4-Ethoxyphenyl)-1-propional

A solution of 3-(4-ethoxyphenyl)-1-propanol (2.90 g, 16.1 mmol, 1.0 equiv) in $CH_2Cl_2$ (50 ml) was added to a suspension of pyridinium chlorochromate (5.21 g, 24.2 mmol, 1.5 equiv) in $CH_2Cl_2$ (150 ml) at rt, and the mixture was stirred for 3.5 h. The reaction mixture was washed with hexane (100 ml) and filtered through silica gel (60 g). The silica gel was eluted with a mixture of hexane and EtOAc (1:1). The combined filtrate was concentrated under vacuum to give 3-(4-ethoxyphenyl)-1-propional (2.51 g, 87.50%) as a slightly yellow oil: $^1$H NMR ($CDCl_3$) δ 9.81 (t, 1H), 7.08 (d, 2H), 6.81(d, 2H), 4.03 (q, 2H), 2.88(m, 2H), 2.74 (m, 2H), 1.40 (t, 3H).

c. N-tert-butyl-C-[2-(4-ethoxyphenyl)ethyl]nitrone

To a solution of 3-(4-ethoxy)phenyl-1-propional (2.51 g, 14.0 mmol, 1.0 equiv) in methanol (100 ml) was added N-tert-butylhydroxylamine (1.38, 15.5 mmol, 1.1 equiv), conc. HCl (5 drops) and the mixture was refluxed for 22 h. The mixture was concentrated under vacuum to give an oil which was purified by flash chromatography (EtOAc:hexane, 2:1) to give N-tert-butyl-C-[2-(4-ethoxyphenyl)ethyl]nitrone (1.44 g, 40.9%) as a yellow solid m.p. 54–57° C. $^1$H NMR (DMSO-$d_6$) δ 7.11 (J=8.4, 2H), 6.97 (t, J=5.6, 1H), 6.83 (d, J=8.4, 2H), 3.97 (q, 2H), 2.72 (t, 2H), 2.57–2.50 (m, 2H), 1.34 (s, 9H), 1.30 (t, 3H).

Example 8

N-tert-butyl-C-[2-(4-benzenesulfonyloxy)phenyl] ethyl]nitrone (Compound 8)

a. 3-[(4-Benzeneulfonyloxy)phenyl]-1-propanol

To a solution of 3-(4-hydroxyphenyl)-1-propanol (3.30 g, 21.7 mmol, 1.0 equiv) in EtOAc (30 ml) was added triethylamine (3.8 ml, 27.1 mmol, 1.25 equiv) and the mixture was stirred for 15 min. Benzenesulfonyl chloride (2.96 ml, 23.2 mmol, 1.07 equiv) was then added drop wise and the mixture was stirred for 3 days. The reaction mixture was poured in 5% KI solution (100 ml, pH=7.0) and extracted with EtOAc. Combined extracts were washed with 5% KI solution, $NaHCO_3$, brine and dried over $MgSO_4$. Concentration of the extracts gave an oil which was purified by column chromatography (EtOAc:hexane 2:1) to give the title compound (3.20 g, 50.5%) as an oil: $^1$H NMR ($CDCl_3$) δ 7.85 (d, 2H), 7.68 (d, 1H), 7.53 (d, 2H), 7.10 (d, 2H) 6.85 (d, 2H), 3.64 (t, 2H), 2.67(t, 2H), 1.89–1.81(m, 2H).

b. 3-[(4-benzenesulfonyloxy)phenyl]-1-propional

A solution of 3-(4-benzenesulfonylphenyl)-1-propanol (3.20 g, 10.9 mmol, 1.0 equiv) in $CH_2Cl_2$ (50 ml) was added to a suspension of pyridinium chlorochromate (3.52 g, 16.4 mmol, 1.5 equiv) in $CH_2Cl_2$ (150 ml) and the mixture was stirred for 18 h at rt. The reaction mixture was washed with hexane (100 ml) and filtered through silica gel (60 g). The silica gel was eluted with mixture of hexane and EtOAc (1:1). The combined filtrate was concentrated under vacuum to give the title compound (3.16 g, 99.50%) as a slight yellow oil. $^1$H NMR ($CDCl_3$) δ 9.68 (t, 1H), 7.84 (t, 3H), 7.67 (t, 2H), 7.20 (d, 2H), 6.90(d, 2H), 4.03 (q, 2H), 2.85–2.71 (m, 3H), 2.52–2.50 (m, 3H).

c. N-tert-butyl-C-[2-(4-benzenesulfonyloxy)phenyl] ethyl]nitrone

To a solution of 3-[(4-benzenesulfonyloxy)phenyl]-1-propional (3.16 g, 10.9 mmol, 1.0 equiv) in methanol (150 ml) was added N-tert-butylhydroxylamine (1.07 g, 12.0 mmol, 1.1 equiv) and the mixture was refluxed for 20 h. The mixture was concentrated under vacuum to give an oil which was purified by flash chromatography (EtOAc:hexane, 1:1) to give the title nitrone (2.57 g, 65.2%) as an off white color oil: $^1$H NMR ($CDCl_3$) δ 7.81 (d, 2H), 7.65 (t, 1H), 7.55–7.46 (t, 2H), 7.11 (t, 2H), 6.89 (d, 2H), 6.77 (d, 1H), 2.83–2.73 (m, 4H), 1.46 (t, 9H).

Example 9

N-tert-butyl-C-[2-(4-acetamidophenyl)ethyl]nitrone (Compound 9)

a. N-(4-Iodophenyl)acetamide

A mixture of 4-iodoaniline (20.00 g, 90.0 mmol, 1.0 equiv) triethylamine (38.4 ml, 274 mmol, 3.0 equiv) and $CH_2Cl_2$ (200 ml) was cooled to 0° C. Acetic anhydride (26.0 ml, 270 mmol, 3.0 equiv) was added drop wise. The reaction mixture was stirred at 0° C. for 10 min, and at rt for 2 h. The volatile materials were removed under vacuum, and the solid residue was dissolved in 30 ml of hot $CH_2Cl_2$. The solution was left to stand in a freezer for 72 h. The separated solid was filtered out and dried under vacuum to give N-(4-iodophenyl)acetamide (20.35 g, 86.6%). $^1$H NMR ($CDCl_3$) δ 7.58–7.28 (d, 2H), 7.25–7.23 (d, 2H), 2.15 (s, 3H).

b. 3-(4'-Acetamidophenyl)-1-propanal

To a mixture of N-(4-Iodophenyl)acetamide (10.8 g, 42 mmol, 1.0 equiv) and DMF (50.0 ml) were added tetrabutylammonium chloride (11.7 g, 42 mmol, 1.0 equiv), $NaHCO_3$ (8.7 g, 105 mmol), and allyl alcohol (4.2 ml, 63 mmol, 1.5 equiv) and the mixture was stirred for 10 min. To the resulting mixture $PdCl_2$ (1.21 g, 9.6 mmol, 0.23 equiv) was added and the mixture was stirred under nitrogen for 45 h. The resulting mixture was extracted with EtOAc (3×100 ml). The combined extracts were washed with 5% HCl, brine, dried over $MgSO_4$ and concentrated under vacuum. The residue was purified by column chromatography (EtOAc:hexane 70:30) to give 3-(4'-Acetamidophenyl)-1-propanal (1.92 g, 23.1%) which was used as such in the next step.

c. N-tert-butyl-C-[2-(4-acetamidophenyl)ethyl]nitrone

To a solution of 3-[(4-acetamidophenyl]-1-propional (1.92 g, 10.0 mmol, 1.0 equiv) in toluene (200 ml) were added N-tert-butylhydroxylamine (1.07 g, 12.0 mmol, 1.2 equiv), p-toluenesulfonic acid (few crystals), and the mixture was refluxed under nitrogen and Dean-Stark trap for 25 h. The mixture was concentrated under vacuum to give an oil which was purified by flash chromatography (EtOAc:hexane 70:30) followed by washing the column with 5% MeOH in EtOAc to give N-tert-butyl-C-[2-(4-acetamidophenyl)ethyl] nitrone (0.770 g 29.4%) as a beige color solid: $^1$H NMR ($CD_3OD$) δ 7.71 (d, 1H, J=8.4), 7.46 (d, 2H), 7.24–7.16 (m, 3H), 2.85–2.72 (m, 4H), 2.10(s, 3H), 1.43(s, 9H).

Example 10

N-tert-butyl-C-[2-(4-benzenesulfonamidophenyl)ethyl]nitrone (Compound 10)

a. 4-benzenesulfonamide-1-iodobenzene

A mixture of 4-iodoaniline (10.00 g, 45.7 mmol, 1.0 equiv), triethylamine (6.36 ml, 45.7 mmol, 1.0 equiv) and CH$_2$Cl$_2$ (200 ml) was cooled to 0° C. Benzenesulfonyl chloride (5.85 ml, 45.7 mmol, 1.0 equiv) was added drop wise. The reaction mixture was stirred at rt for 3 h and then concentrated under vacuum to give a white solid (8.45 g, 51.5%) which was dried and used as such in the next step.

b. 3-(4-benzenesulfonamidophenyl)-1-propional

To a mixture of 4-benzene sulfonamido-1-iodobenzene (8.45 g, 23.5 mmol, 1.0 equiv) in DMF (50.0 ml) were added tetrabutylammonium chloride (6.54 g, 23.5 mmol, 1.0 equiv), NaHCO$_3$ (4.94 g, 58.8 mmol), and allyl alcohol (2.05 ml, 35.3 mmol, 1.5 equiv) and the mixture stirred for 10 min. To the resulting mixture PdCl$_2$ (0.95 g, 5.4 mmol, 0.23 equiv) was added and mixture stirred under nitrogen for 70 h. The resulting mixture was extracted with EtOAc. The combined extracts were washed with 5% HCl, brine, dried over MgSO$_4$ and concentrated under vacuum to give an oil. The residue was purified by column chromatography (EtOAc:hexane 1:1) to give 3-(4-benzenesulfonamidophenyl)-1-propional (4.00 g, 58.8%) as a light yellow oil which was used as such in the next step.

c. N-tert-butyl-C-[2-(4-benzenesulfonamidophenyl)ethyl]nitrone

To a solution of 3-(4-benzenesulfonamidophenyl)-1-propional (1.04 g, 3.59 mmol, 1.0 equiv) in methanol (50 ml) was added N-tert-butylhydroxylamine (0.35 g, 3.95 mmol, 1.1 equiv), and the mixture refluxed for 18 h. The mixture was concentrated under vacuum to give a flaky yellow solid which was purified by column chromatography (EtOAc:hexane 1:1) to give N-tert-butyl-C-[2-(4-benzenesulfonamidophenyl)ethyl]nitrone (0.830 g, 64.3%) as a beige color solid m.p. 160° C.: $^1$H NMR (CD$_3$OD) δ 7.73 (d, 1H), 7.56–7.36 (m, 3H), 6.99 (d, 4H), 6.80 (t, 1H), 2.78–2.64 (m, 4H), 1.46 (s, 9H).

Example 11

N-tert-butyl-C-[2-(4-N,N-Dibenzenesulfimidophenyl)ethyl]nitrone (Compound 11)

a. 4-(N,N-Dibenzenesulfimido)-1-iodobenzene

A mixture of 4-iodoaniline (10.00 g, 45.7 mmol, 1.0 equiv) and triethylamine (19.1 ml, 137 mmol, 3.0 equiv) and CH$_2$Cl$_2$ (200 ml) was cooled to 0° C. Benzenesulfonyl chloride (17.3 ml, 135 mmol, 3.0 equiv) was added drop wise. The reaction mixture was left to stir at rt for 2 h. The resulting mixture was concentrated under vacuum to give a yellow solid. To this solid was added EtOAc (200 ml), and a white insoluble solid was obtained. The white solid, with the help of water, was dissolved in CH$_2$Cl$_2$. The organic layer was washed with aq. NaHCO$_3$, brine, dried over MgSO$_4$ and concentrated under vacuum to give 4-(N,N-Dibenzenesulfimido)-1-iodobenzene (16.51 g, 72.35%) as a white solid: $^1$H NMR (CDCl$_3$) δ 7.93–7.90 (m, 4H), 7.70–7.65 (m, 4H), 7.57–7.52 (m, 4H), 6.75–6.71 (m, 2H).

b. 3-[(4-(N,N-Dibenzenesulfimido)phenyl]-1-propional

To a solution of 4-(N,N-di-benzenesulfimido)-1-iodobenzene (10.0 g, 20.0 mmol, 1.0 equiv) in DMF (50.0 ml) was added tetrabutylammonium chloride (5.57 g, 20.0 mmol, 1.0 equiv), NaHCO$_3$ (4.20 g, 50.0 mmol), and allyl alcohol (1.74 g, 30.0 mmol, 1.5 equiv) and the mixture stirred for 10 min. To the resulting mixture PdCl$_2$ (0.81 g, 4.6 mmol, 0.23 equiv) was added and the mixture was then stirred under nitrogen for 70 h. The resulting mixture was extracted with EtOAc and combined extracts were washed with 5% HCl, brine, dried over MgSO4 and concentrated under vacuum to a solid which was purified by column chromatography (EtOAc:hexane 1:1) to give 3-[(4-(N,N-dibenzenesulfimido)phenyl]-1-propional (7.24 g, 84.3%) as a white solid. $^1$H NMR (CDCl$_3$) δ 9.82 (s, 1H), 7.92 (d, 2H), 7.69–7.64 (m, 2H), 7.56–7.51 (m, 4H), 7.16 (d, 2H), 6.93 (d, 2H), 2.99–2.78 (m, 4H).

c. N-tert-butyl-C-[2-(4-N,N-Dibenzenesulfimidophenyl)ethyl]nitrone

To a solution of 3-[(4-N,N-dibenzenesulfimido)phenyl]-1-propional (2.00 g, 4.0 mmol, 1.0 equiv) and methanol (100 ml) was added N-tert-butylhydroxylamine (0.40 g, 4.5 mmol, 1.1 equiv), and the resulting mixture was refluxed for 18 h. The mixture was concentrated under vacuum to give a white glassy solid which was purified by column chromatography (EtOAc:hexane=(1:1), then with EtOAc to give N-tert-butyl-C-[2-(4-N,N-di-benzenesulfimidophenyl)ethyl]nitrone (1.42 g, 71.0%) as an off-white solid m.p. 44–47° C.: $^1$H NMR (CD$_3$OD) δ 7.86–7.59 (m, 10H), 7.26–7.20 (m, 3H), 6.92 (d, 2H), 2.96–2.72 (m, 4H), 1.43 (s, 9H).

Example 12

N-tert-butyl-C-(5-phenylpentyl)nitrone (Compound 12)

a. 6-phenyl-1-hexanal

A solution of 6-phenylhexanol (5.00 g, 28.0 mmol, 1 equiv) in CH$_2$Cl$_2$ (10 ml) was added to a solution of pyridinium chlorochromate (9.07 g, 42.1 mmol, 1.5 equiv) in CH$_2$Cl$_2$ (100 ml) at rt, and the mixture was stirred for 3.5 h. The reaction mixture was diluted with hexane and filtered through silica gel (20 g). The silica gel was eluted with a mixture of hexane and EtOAc (1:1). The combined filtrate was concentrated under vacuum to give 6-phenyl-1-hexional as a colorless oil, which was used as such for the next step. $^1$H NMR (CDCl$_3$) δ 9.75 (t, 1H), 7.28–7.14 (m, 5H), 2.61 (T, 2H), 2.44–2.38 (m, 2H), 1.71–1.58 (m, 5H), 1.42–1.30 (m, 2H).

b. N-tert-butyl-C-(5-phenylpentyl)nitrone

To a solution of 6-phenyl 1-hexanal (4.93 g, 28.0 mmol, 1 equiv) in methanol (50 ml) was added N-tert-butylhydroxylamine (3.00 g, 33.6 mmol, 1.2 equiv), and the mixture was stirred at rt. for 4 h. Concentration of the mixture gave a light colored oil which was purified by flash chromatography (EtOAc) to give N-tert-butyl-C-(5-phenylpentyl)nitrone (4.39 g, 89.0%) as a colorless oil: $^1$H NMR (CD$_3$OD) δ 7.28–7.11 (m, 6H), 2.66–2.24 (m, 4H,), 1.72–1.24 (m, 15H).

Example 13

N-tert-butyl-C-[2-(4-isopropylphenyl)-1-methyethyl]nitrone (Compound 13)

To a mixture of [2-methyl-3-(4-isopropylphenyl)-propionaldehyde] (3.0 g, 15.8 mmol, 1.0 equiv), N-tert-butylhydroxylamine (1.76 g, 19.7 mmol, 1.3 equiv) and toluene (60 ml) was added p-TsOH (50 mg), and the mixture was stirred at rt for 18 h. Removal of the solvent under reduced pressure gave a solid which was purified by column chromatography (EtOAc:hexane 1:1) to give N-tert-butyl-C-[2-(4-isopropylphenyl)-1-methyethyl]nitrone (1.04 g, 25.18%) as a white solid: $^1$H NMR (CDCl$_3$) δ 7.12 (d, J=1.0, 4H), 6.63 (d, J=7.2 1H), 3.47–3.31 (m, 1H), 2.89–2.80 (m, 2H), 2.71–2.63 (dd, 1H), 1.44 (s, 9H), 1.25 (d, J=6.9, 3H).

Example 14

N-tert-butyl-C-(4-phenylpropyl)nitrone
(Compound 14)

To a mixture of 3-phenylbutyraldehyde (10.0 g, 67.5 mmol, 1.0 equiv) and benzene (150 ml) and silica gel (5 g) was added N-tert-butylhydroxylamine (7.22 g, 81.0 mmol, 1.2 equiv) and the mixture stirred at rt for 18 h. The mixture was filtered and the filtrate was concentrated under vacuum to give N-tert-butyl-C-(2-phenylpropyl)nitrone (13.74 g, 92.80%) as a light yellow oil. $^1$H NMR (CDCl$_3$) δ 7.33–7.19 (m, 5H), 6.65 (t, 1H), 3.18–3.04 (m, 1H), 2.90–2.65 (m, 2H), 1.40 (s, 9H), 1.34–1.32 (d, 3H).

Example 15

N-tert-butyl-C-[1-(4-tert-butyl phenyl)propyl]nitrone
(Compound 15)

To a mixture of 3-(4-tert-butylphenyl)-butyraldehyde (10.0 ml, 46.5 mmol, 1.0 equiv) and methanol (100 ml) was added N-tert-butylhydroxylamine (4.97 g, 55.8 mmol, 1.2 equiv), conc. HCl (10 drops) and the mixture was stirred at rt for 20 h. The mixture was filtered and concentrated under vacuum to give N-tert-butyl-C-[1-(4-butylbenzyl)ethyl]nitrone (12.30 g, 96.00%) as a colorless oil. $^1$H NMR (CDCl$_3$) δ 7.30–7.27 (d, 2H), 7.13–7.10 (d, 2H), 6.65–6.62 (d, 1H), 3.47–3.33 (m, 1H), 2.87–2.64 (m, 2H), 1.44 (s, 9H), 1.87–1.06 (d, 3H).

Example 16

N-tert-butyl-C-[1-2-(4-methoxyphenyl)methylethyl]nitrone (Compound 16)

To a mixture of Canthoxal (5.0 ml, 30.5 mmol, 1.0 equiv) and benzene (200 ml) was added N-tert-butylhydroxylamine (4.97 g, 55.8 mmol, 1.2 equiv), silica gel (10 g), and the mixture was then stirred at rt for 17 h. The mixture was filtered and the filtrate was concentrated under vacuum to give a colorless oil. The product was purified by column chromatography (EtOAc:hexane 1:1) to give the title compound (5.12 g, 83.10%) as a colorless oil. $^1$H NMR (CDCl$_3$) δ 7.12–7.08 (d, 2H), 6.84–6.80 (d, 2H), 6.63–6.61 (d, 1H), 3.78 (s, 3H), 3.42–3.28 (m, 1H), 2.86–2.79 (dd, 1H), 2.68–2.60 (dd, 1H), 1.45 (s, 9H), 1.07–1.05 (d, 3H).

Example 17

N-tert-butyl-C-phenylmethyl nitrone
(Compound 17)

To a mixture of phenyl-acetaldehyde (1.20 g, 10.00 mmol) and chloroform (50 ml) was added N-tert-butylhydroxylamine (1.07 g, 12.00 mmol) followed by 5 drops of conc. HCl. The mixture was stirred at rt for 18 h. The mixture was concentrated under vacuum to give an oil. The residue was purified by column chromatography (hexane: EtOAc=1:1) followed by EtOAc to give the title compound as a white solid: Yield: 80%, m.p. 143° C.: $^1$H NMR (CDCl$_3$) δ 7.38 (m, 5H), 6.90 (s, 1H), 4.95 (dd, 2H), 1.25 (s, 9H).

Example 18

N-Cyclohexyl-C-(2-phenylethyl)nitrone
(Compound 18)

To a mixture of 3-phenylpropionaldehyde (5.0 g, 37.3 mmol, 1.0 equiv.) and CHCl$_3$ (150 ml) was added N-cyclohexylhydroxylamine (4.30 g, 41.0 mmol, 1.1 equiv) and p-TsOH (few crystals) and the resulting mixture was refluxed under nitrogen for 22 h. Removal of the solvent an oil was obtained which was purified by flash chromatography (hexanes: EtOAc 1:1) to give N-cyclohexyl-C-(2-phenylethyl)nitrone (6.41 g, 74.4%) as a white solid, m.p. 97.2° C.: $^1$H NMR (CDCl$_3$) δ 7.33–7.19 (m, 5H,), 6.69–6.65 (t, 1H, Ar—H), 3.67–3.56 (m, 1H), 2.91–2.78 (m, 4H), 1.97–1.63 (m, 7H), 1.37–1.10 (m, 3H).

Example 19

N-tert-butyl-C-[4-phenylbutyl]nitrone
(Compound 19)

To a mixture of 5-[phenyl-pentanal (1.62 g, 10 mmol, 1.0 equiv) and methanol (50 ml) was added N-tert-butylhydroxylamine (0.93 g, 10.43 mmol, 1.25 equiv) followed by 10 drops of conc. HCl. The mixture was stirred at rt for 18 h. The mixture was concentrated under vacuum to yield a light colored oil. The residue oil was purified by column chromatography (hexane:EtOAc 1:1) followed by EtOAc to give the title compound as a lightly colored oil: Yield: 39%: $^1$H NMR (CDCl$_3$) δ 7.20 (m, 5H), 6.94 (d, 1H), 2.50 (m, 4H), 1.60 (m, 4H), 1.46 (s, 9H).

Example 20

N-tert-butyl-C-[1-(phenyl)ethyl)nitrone
(Compound 20)

To a mixture of 2-phenyl-propional (1.34 g, 10 mmol, 1.0 equiv) and methanol (50 ml) was added N-tert-butylhydroxylamine (0.93 g, 10.43 mmol, 1.25 equiv) followed by 10 drops of conc. HCl. The mixture was stirred at rt for 18 h. The mixture was concentrated under vacuum to yield a light colored oil. The residue oil was purified by column chromatography (hexane:EtOAc 1:1) followed by EtOAc to give title compound as solid. Yield: 71%, m.p. 56° C.: $^1$H NMR (DMSOd$_6$) δ 7.30 (s, 5H), 7.15 (s, 1H), 4.12 (m, 1H), 1.30 (s, 3H), 1.48 (s, 9H).

Example 21

N-tert-butyl-C-[2–3,5-di-tert-butyl-4-hydroxyphenyl)ethyl]nitrone (Compound 21)

To a mixture of 3-[3,5-di-tert-butyl-4-hydroxyphenyl] propional (2.00 g, 7.62 mmol, 1.0 equiv) and methanol (50 ml) was added N-tert-butylhydroxylamine (1.02 g, 11.44 mmol, 1.25 equiv) followed by 10 drops of conc. HCl. The mixture was stirred at rt for 18 h. The mixture was concentrated under vacuum to yield white solid. The residue was purified by column chromatography (hexane:EtOAc 1:1) followed by EtOAc to yield the title compound (1.96 g, 80%) as a white solid: Yield: 80%, m.p. 149° C.: $^1$H NMR (CDCl$_3$) δ 6.97 (s, 2H), 6.84 (s, 1H), 2.75 (m, 4H), 1.45 (s, 9H), 1.40 (s, 18H).

Example 22

N-tert-butyl-C-[2–3,5-di-tert-butyl-4-hydroxyphenyl)methyl]nitrone (Compound 22)

To a solution of 3,5-di-tert-butyl-4-hydroxy-phenyl)-1-ethanal (1.50 g, 2.41 mmol,) and methanol (50 ml) was added N-tert-butylhydroxylamine (280 mg, 3.14 mmol) and the resulting mixture was refluxed under nitrogen for 6 h. The reaction mixture was concentrated under vacuum to give an oil which was purified by flash chromatography (hexane:EtOAc=1:1) to give N-tert-butyl-C-[2-(3,5-di-tert-butyl-4-hydroxyphenyl)methyl]nitrone as a solid.: Yield.: 31%, m.p. 124° C. $^1$H NMR (CDCl$_3$) δ 7.00 (s, 2H), 6.96 (m, 1H), 3.75 (d, 2H), 1.51 (s, 9H), 1.41 (s, 18H).

Example 23

N-tert-butyl-C-[4-methoxy-phenyl)propyl]nitrone (Compound 23)

To a solution of 4-(4-methoxy-phenyl)-1-butanal (0.43 g, 2.41 mmol,) and methanol (50 ml) was added N-tert-butylhydroxylamine (280 mg, 3.14 mmol) and the resulting mixture was refluxed under nitrogen for 6 h. The reaction mixture was concentrated under vacuum to give an oil which was purified by flash chromatography (hexane:EtOAc=1:1) to give the title compound as a solid.: Yield.: 53%, $^1$H NMR (CDCl$_3$) δ 7.1(m, 2H), 6.81 (m, 2H), 6.70 (m, 1H), 3.80 (s, 3H), 2.70–2.45 (m, 4H), 1.84–1.75 (m, 2H), 1.42 (s, 9H).

Example I

Analgesia Testing

The purpose of the following studies was to determine whether test compounds had analgesic activity in a chronic constriction injury (CCI) rat model of peripheral neuropathy. Neuropathic rats were treated with PBN, and other test compounds or 2.5% DMSO in 1.0% MC as a vehicle and tested in a cold allodynia assay to evaluate nociceptive responses.

Experimental Design

Figure 2:
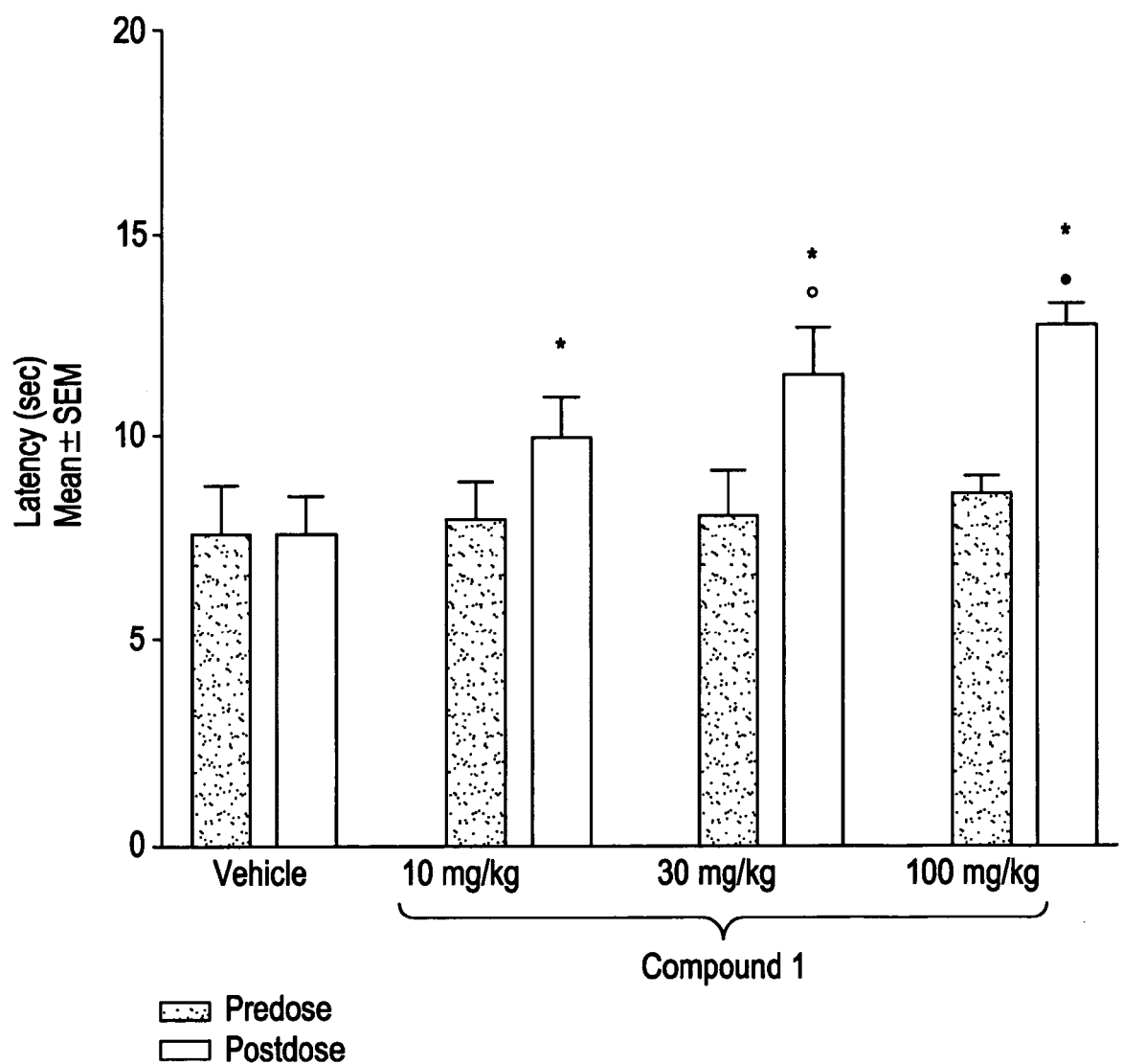
FIG. 2: A graph showing treatment of CCI Rats with Compound 1 increases latency in cold allodynia assay of chronic constriction injury (CCI). Rats exhibiting latency to cold stimulus were treated with vehicle and different concentrations of Compound 1 (10, 30, 100 mg/kg, p.o.). Animals were again tested 90 min post-dose. Pre-dose and post-dose average scores are shown. Treatment with Compound 1 at 10, 30, & 100 mg/kg significantly increased latency time above the pre-dose scores (*$p<0.05$ vs. pre-dose score, Wilcoxon test). Kruskal-Wallis test indicated significant post-dose latency score over vehicle (n=10), in animals treated with Compound 1 at 30 mg/kg ($p<0.05$ vs. vehicle post-dose, n=10, Dunn's test post hoc) and 100 mg/kg ($p<0.01$ vs. vehicle post-dose, n=10, Dunn's test post hoc).

One week prior to the cold allodynia assay, CCI rats were prepared as follows. Male Sprague Dawley rats (158–224 g) had their right sciatic nerve loosely ligated under aseptic conditions. To observe the cold allodynia response, their paw withdrawal latency response was determined by placing rats in a cold water bath (2–4° C., 2.5 cm deep). Under these conditions, normal rats do not exhibit pain or withdraw their feet. Rats rendered neuropathic in the right limb display an exaggerated withdrawal response on the neuropathic side (right rear limb). For the cold allodynia assay, two pre-dose latency times to cold were recorded. The end point was an exaggerated removal of the paw from the water. Rats which did not demonstrate a consistent neuropathic response were removed from the study. The remaining rats were divided into treatment groups. Two separate latency times were obtained for each rat before the dose of each drug. In the first study shown in FIG. 1, rats were then dosed with Compound 1 (30 mg/kg, po) or PBN (100 mg/kg, po) as a suspension in Veh, or Veh alone (1 ml/kg, po). In the second study shown as FIG. 2, three different doses of Compound 1 (10, 30, 100 mg/kg, po) were administered to CCI rats. In both studies, latency to withdraw the ligated leg up above water level was recorded using an electronic timer. The tester was blinded to the animal's treatment group at the time of testing.

Maximum time of latency in any trial was 20 sec. Statistical significance was assessed for paired groups (pre-dose vs. post-dose) using a Wilcoxon test and between non-paired groups using a Kruskal-Wallis with a Dunn's test post-hoc. A probability value of $p<0.05$ was identified as statistically significant.

Example II

Adjuvant Assay

In this example, the ability of compounds of formula I to reduce adjuvant-induced footpad edema in rats is demonstrated. This assay is a model for chronic inflammation. See, for example, B. M. Weichman, "Rat Adjuvant Arthritis: A Model of Chronic Inflammation," *Pharmacological Methods in the Control of Inflammation*, 363–380 (1989) and references cited therein.

Figure 3:
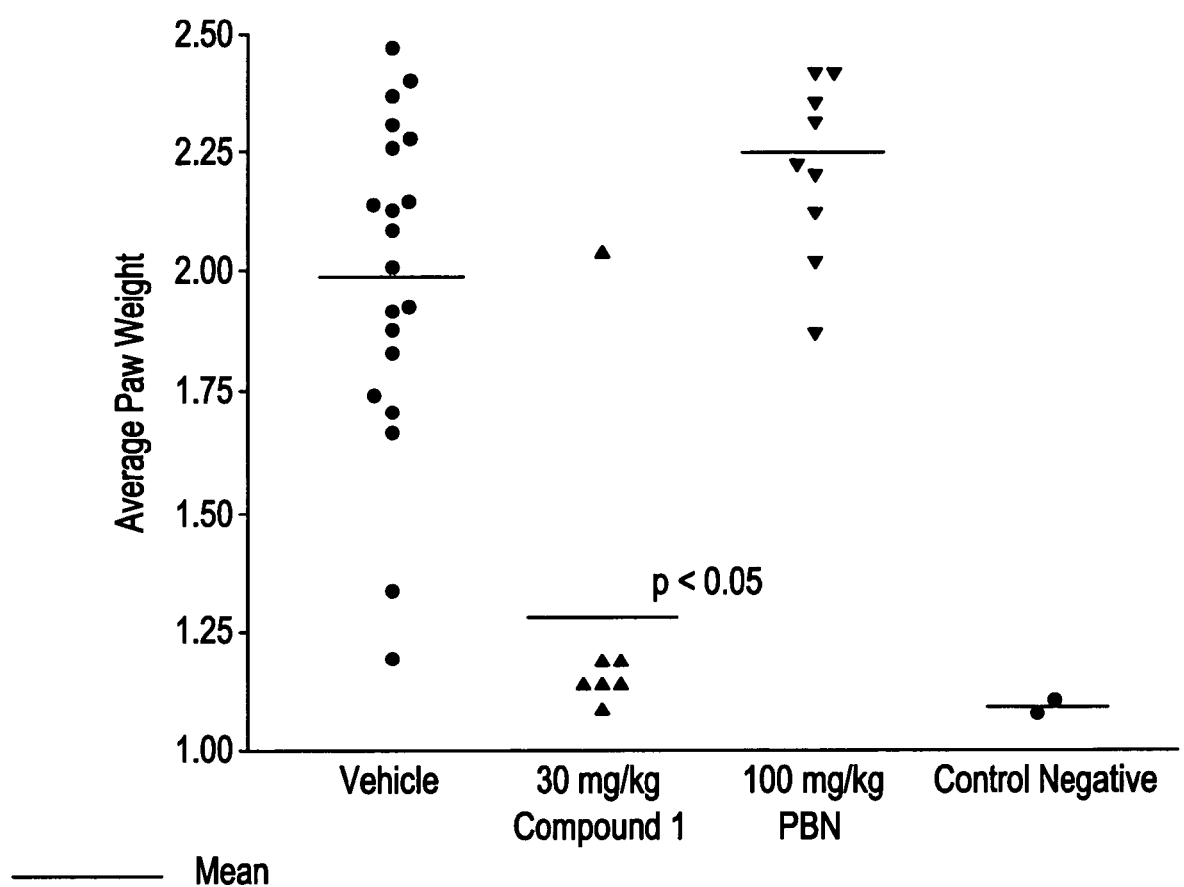
FIG. 3: A graph showing the paw volume differences after treatment with test compounds in the rat collagen assay as described above. Note the unexpected activity of Compound 1 in this model compared with N-tert-butyl phenyl nitrone (PBN). PBN is inactive in this model when tested at 100 mg/kg.

In this assay, Male Lewis rats weighing between 180–220 g were lightly anesthetized with an ip injection of 30 mg/kg of sodium pentobarbital (50 mg/ml). Desiccated *Mycobacterium butyrium* (Difco, 20 mg/ml) suspended in mineral oil was injected (50 μL) at both sides of the base of the tail under the skin. A line was tattooed on both rear paws at 5 mm above the angle of the ankle. The paw volumes, under the line, were measured by volume displacement using a plethysmometer (Ugo Basile) at the day of adjuvant injection (day 0) and on day 14. On day 14, animals with paw volumes equal to the mean of paw volumes ±SD were randomized into treatment groups. Rats which fell outside ±1 SD were not used in the experiment. One group received vehicle (1% methyl cellulose) by the po route and the other group received indomethacin (3 mg/kg suspended in 1% methyl cellulose). Dosing began on day 14, and continued until final assessment on day 21 post-adjuvant injection. A separate group, which did not receive adjuvant or test compound, was also monitored as a control. This group has a slightly positive volume increase when paw volumes on day 21 are subtracted from day 0 values due to growth of the rat. Indomethacin (3 mg/kg, po), a known anti-inflammation compound, significantly reduced paw volume as compared to vehicle controls. Compounds reducing paw volume by at least about 30% compared to vehicle control group were considered effective in this test. Representative results are shown in FIG. 3.

Example III

Collagen Arthritis Assay

In this example, the ability of compounds of formula I to reduce collagen footpad edema in rats is demonstrated. This assay is commonly used to screen and evaluate anti-inflammatory drug candidates. See, for example, Larsson et al., *Arthritis & Rheumatism*, 33:693–701, 1990 and references cited therein.

For these experiments, Female DA rats (7–8 weeks of age) were immunized with Type II collagen derived from bovine nasal septum as described in Cremer et al., *J. of Immunology*, 149:1045–1053, 1992. The collagen was dissolved and administered with incomplete Freund's adjuvant.

Standard precautions were taken to avoid denaturing the collagen before its administration such as keeping the solution cold during preparation. Rats were immunized in the base of the tail on day 0. Dosing began on day 10 with rat paws weighed and volumes taken on day 21. The arthritis was evaluated by comparing paw weights and/or paw volumes at day 21. Compounds reducing paw weight or paw volumes by at least about 30% compared to the controls were also considered effective in this assay. Representative results are shown in FIG. 4.

Assay Results

Each compound of formula I that was tested in the above assays was found to be effective in the analgesic, adjuvant and/or collagen assay. For example, N-tert-butyl-C-(2-phenylethyl)nitrone was significantly active in a model of painful peripheral neuropathy at 10 mg/kg, po. Further, it was significantly active in a rat collagen model. These findings are totally unexpected since a closely related structure such as N-tert-butyl phenyl nitrone (PBN) is inactive or nearly so in the above assays. PBN was tested in all of the above assays and was found to be completely inactive.

Figure 4:
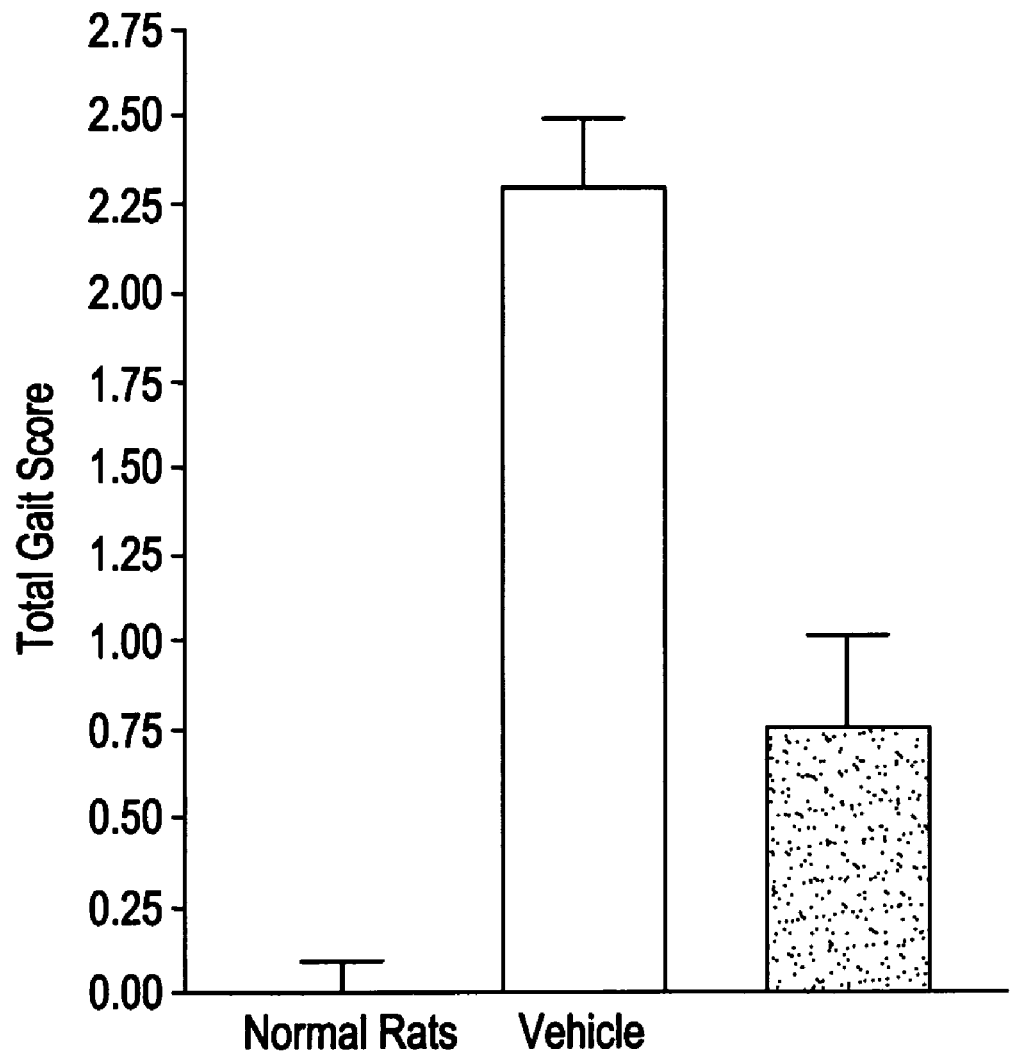
FIG. 4: A graph showing that Compound 1 has activity as an analgesic in the rat collagen model. Total gait scores as an index of pain was measured in this study. Gait scores are known to be correlated with pain in this model. The lowering of total gait scores indicates a relief from pain.

In addition, Compound 1 showed significant activity in the collagen arthritis assay by decreasing total gait scores (see FIG. 4). This activity is correlated with reduction of pain in this model, and indicates that compounds of this series have analgesic activity and well as anti-inflammatory activity in arthritis. Thus compounds such as Compound 1 have both anti-inflammatory and analgesic activity.

Example IV

A Taxol model was employed for the studies of analgesic effects of the nitrone compounds of the invention. The following example presents the results of this test of the activity of Compound 14 against neuropathic pain. The protocol followed in this example is described below.

a. Taxol Induced Neuropathic Pain Model

Taxol is a chemotherapeutic reagent for treatment of cancer patients. Cancer patients under Taxol chemotherapy can develop neuropathic pain, with a symptom of severe mechanical allodynia, so that a light touch (non-noxious stimulus in a normal condition) becomes painful. Taxol has been shown to interact with beta-tubulin, hence functions as a microtubule stabilizer. Recent studies have shown that Taxol is involved in TNF-alpha release in microglia cells. As one of the clinically relevant models, Taxol-induced neuropathic pain was developed in mice and rats. It is believed that small-diameter high threshold nociceptive C-fibers in the peripheral sensory nervous systems are largely, if not exclusively, affected in the Taxol-induced neuropathic pain models.

In this series of experiments, five-week old, male C57Bl/6 mice were purchased from Charles River and housed at the Renovis animal facility in South San Francisco. Mice were trained for one week in an enclosure made of Plexiglas with dimensions of 2 in×2.5 in×3.5 in (W, H, and L) with a meshed metal support. The baseline of response to mechanical stimulus was measured using a von Frey Filament (0.6 g=3.84 mN). Normally, the baseline response is between 0 to 40%.

Taxol was dissolved (1 mg/ml) in 50% Cremophor EL and 50% alcohol, and freshly diluted with saline to the final concentration of 0.2 mg/ml in 10% Cremophor EL, 10% alcohol. Mice were administered Taxol at 1 mg/kg of body weight, via i.p. daily, while the animals of the control group received vehicle (10% Cremophor EL and 10% alcohol in saline).

Animals receiving this daily dose of Taxol will develop neuropathic pain. The mechanical allodynia was measured at day 7, 8, or 14 after Taxol administration.

b. Preparation of Solution of Compound 14

A quantity of 200 mg of compound 14 (Example 14) was dissolved in 0.4 ml of 100% DMSO to yield a concentration of 500 mg/ml, and was kept at 4° C. until use. Methylcellulose was dissolved in deionized-distilled water to yield a concentration of 1%. The freshly prepared meythlcellulose was used to make a suspension of the compound, 10 mg of compound in 2.5% DMSO (V/V) and 1% methylcellulose. The suspension was sonicated for 6 min with a 5 second interval every 30 seconds before administration to animals.

c. Compound Administration and Behavior Measurements

A quantity of 50 mg/kg (body weight) compound or vehicle (2.5% DMSO and 1% methylcellulose), 100 µl/20 g (body weight) was given to animals via gavage feeding procedure in a randomized, blinded fashion. The animals were then placed in the enclosure for assay. Mechanical allodynia was measured with von Frey filament (0.6 g=3.84 MN) at various times after administration. The results of the administration of the compound are shown in FIG. 5.

d. Compound 14 Inhibits Mechanical Allodynia in Neuropathic Pain Model

Figure 5:
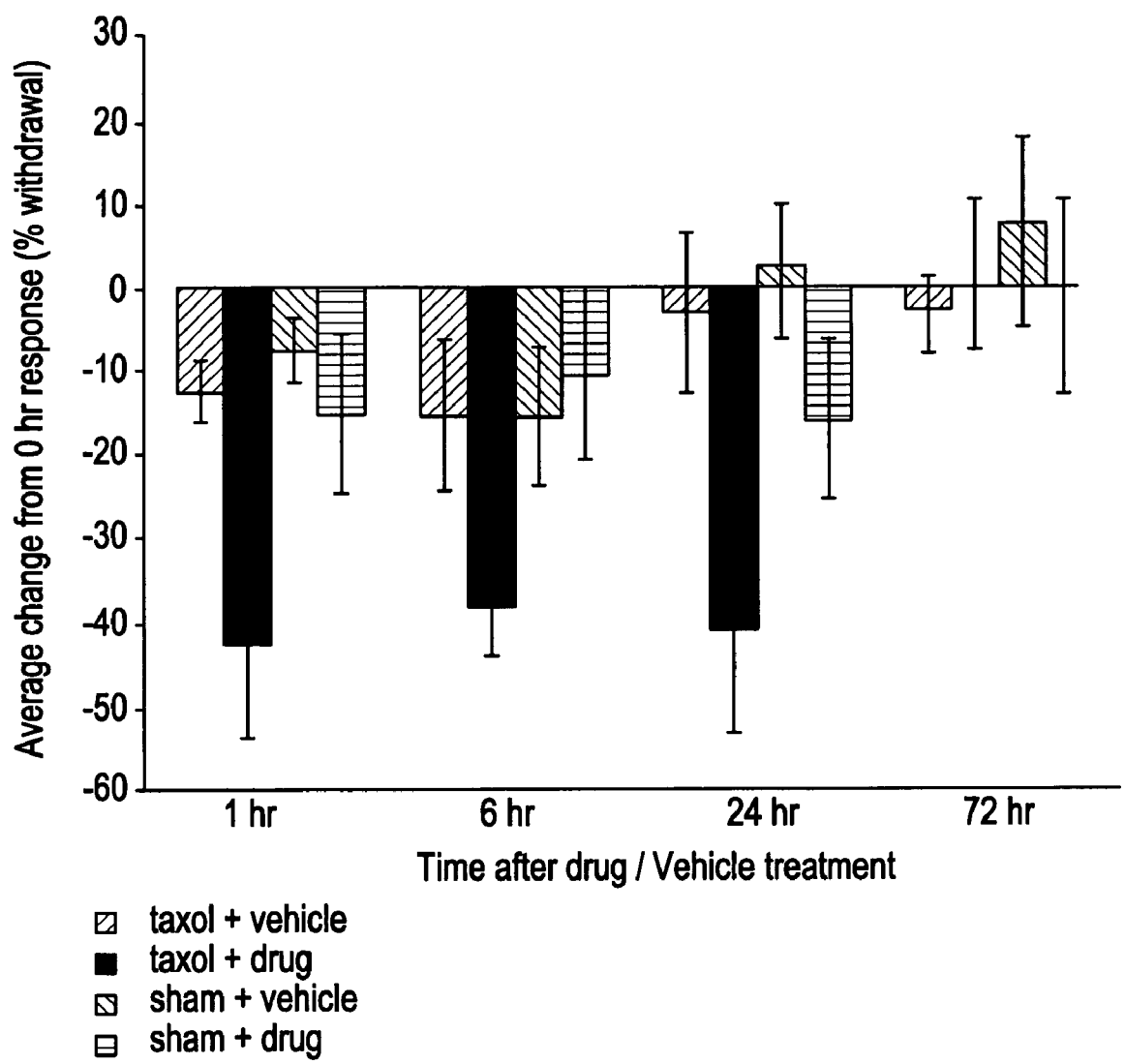
FIG. 5: A graph showing that Compound 14 has activity preventing Taxol-induced pain in a rat model.

Referring to FIG. 5, baseline in the group of animals was measured as 25+/−4% (n=24, ±SEM) before induction of neuropathic pain with Taxol (or sham treatment), where the response was measured with a von Frey filament (0.6 g=3.84 mN) as the percent of trials a withdrawal response is observed after probing with the filament. The higher the percentage, the greater the inferred pain.

Sixteen animals were treated with Taxol daily to induce neuropathic pain. Mechanical allodynia was assayed at day 8; average withdrawal response was measured as 81±5% (n=16, ±SEM). Sixteen animals were treated with matching vehicle to create sham animals. The Taxol and sham animals were then separated randomly into two groups of 8 animals each for drug vs. vehicle testing. Withdrawal responses to a von Frey filament probe were measured at 1, 6, 24, and 72 hours post-administration of drug or vehicle control, and averaged for each animal. FIG. 5 shows the change at these timepoints in average withdrawal percentage relative to response prior to drug or vehicle adminstration (error bars reflect SEM). Negative values reflect a reduction in inferred pain.

Example V a. Neuropathic Pain Testing of Additional Compounds

In this series of experiments, further compounds of the present invention were tested for possible activity in the treatment of neuropathic pain. The tests in particular, included the Taxol induced neuropathic pain model used in Example IV, and a spinal nerve ligation model (Chung model) that uses rats. The respective tests are discussed below.

b. Taxol Induced Neuropathic Pain Model

For mouse neuropathic pain studies, C57Bl/6 strain, five-weeks old male mice were obtained from Charles River, San Diego, Calif. A total of 120 mice were used for the studies. 4 mice per cage were housed under standard conditions with 12-hour light and 12-hour dark cycles (in Renovis, Inc, South San Francisco facility). For rat neuropathic pain studies, male Sprague-Dawley rats, with body weights ranging from 180–200 grams, were obtained from Harlan. A total of 42 rats were used for this study. 3 rats per cage were housed under standard conditions with 12-hour light and 12-hour dark cycles (Renovis, Inc. Redwood City facility).

von Frey Filament sets were purchased from Stoeling. Customized mouse enclosures [with a dimension of 2.5 inches×2.5 inches×3 inches (W×H×L)] and rat enclosures

[with a dimension of 3.5 inches×4 inches×10 inches (W×H× L)] were obtained from IITC for mechanical allodynia tests.

Taxol was prepared for i.p administration as follows. For the Taxol-induced neuropathic pain mouse model, 1 mg of Taxol was dissolved in 50% of Cremophor EL/50% of absolute ETOH (volume/volume), and kept in the dark at 4° C. no longer than 3 days. Prior to administration, the Taxol solution was diluted with saline (1 volume of 1 mg Taxol solution in Cremophor EL/ETOH (50:50) was added with 4 volumes of saline) to give 0.2 mg/ml of Taxol in 10% Cremophor EL, 10% ETOH and 80% of saline. 100 uL of Taxol solution per 20 grams body weight of mouse was administered to mouse via i.p. to give a dose of 1 mg/kg (body weight).

For the Taxol-induced neuropathic pain rat model, 5 mg of Taxol was dissolved in 50% of Cremophor EL/50% of absolute ETOH (volume/volume), and kept in the dark at 4° C. no longer than 3 days. Prior to administration, the Taxol solution was diluted with saline (1 volume of 1 mg Taxol solution in Cremophor EL/ETOH (50:50) was mixed with 4 volumes of saline) to give 1 mg/ml of Taxol in 10% Cremophor EL, 10% ETOH and 80% of saline. 200 uL of Taxol solution per 200 grams body weight based on the rat model, was administered to each mouse via i.p. to give a dose of 1 mg/kg (body weight).

c. Preparation of Formulations of Compounds for Testing

A methylcellulose formulation for oral gavage feeding of nitrone compounds in rats was prepared as follows. 1% of methylcellulose was dissolved in water and kept at 4° C. 50 mg/ml and 20 mg/ml of compound/1% methylcellulose suspension was made by 12 cycles of sonication, each cycle lasting 30 seconds with 5 second intervals on ice. 1 ml per kg of body weight of either 50 mg/ml or 20 mg/ml of compound was administered to rats via oral gavage feeding (p.o.), to yield dose of either 50 mg/kg (body weight) or 20 mg/kg (body weight). The same corresponding volume, of 1% methylcellulose was used as vehicle control.

Compound 14 and Compound 23 were prepared for i.p. administration as follows. 250 mg/ml of each of the compounds to be tested, was dissolved in a mixture of Cremophor EL/alcohol (90:10) (volume:volume), respectively, by brief sonication on ice, followed by further 10-fold dilution in saline solution (9% Cremophor EL; 1% ETOH and 90% saline) to give a final concentration of 25 mg/ml. before injection. 1 ml/kg (body weight) of compound solution was administered via i.p. to rats, to yield a dose of 25 mg/kg.

c. Taxol-Induced Neuropathic Pain Model in Mice

Accordingly, C57B1/6 male mice were preconditioned (trained) in the enclosure one hour per day in the morning for a week prior to the baseline measurement. The baseline response to the mechanical stimulus was measured using a von Frey filament with 0.6 grams of force (von Frey number 3.84). Briefly, the von Frey filament, as indicated above, was applied to the plantar area of the right hind paw of the mouse. The frequency of paw withdrawal was calculated in terms of percentage response, where an increasing or higher percentage indicates more pain while a reduced or lower percentage indicates less pain.

Based on experience with the C57B1/6 strain of adult male mice, animals with baseline no greater than 40% of response were included in the further studies, while those with greater than 40% of paw withdrawal response to this particular force of stimulus, known as spontaneous mechanical allodynia, were discarded from these studies. The paw withdrawal behavior includes, licking the stimulated paw, vigorously shaking the paw and active avoidance upon application of innocuous mechanical stimuli. For those mice without spontaneous mechanical allodynia, Taxol was administered, as indicated in the previous section, to the mice daily, 5 days a week, for longer than a week period.

Generally, mice treated with daily i.p. administration of 1 mg/kg (body weight) of Taxol develop relatively stable mechanical allodynia, neuropathic pain, on day 9 and thereafter. Prior to compound administration, the responses of mice to 0.6 gram of von Frey filament were measured for two consecutive days in the morning. Only those mice with a paw withdrawal response to this particular von Frey filament stimulus no less than 60%, counted as mechanical allodynia, were included for later compound tests.

d. Results

Eight nitrone compounds were tested in a Taxol-induced neuropathic pain model in mice (Compounds 1, 4, 6, 7, 14, 15 and 21) at 50 mg/kg (body weight) with a single dose and the mechanical allodynia was measured at 1, 6, 24, up to 48 or 72 hours postdosing. Compound 1 showed analgesic effect 1 hour postdosing. Compound 14 showed significant reduction of mechanical allodynia at 1 hour post dosing up to 24 hour postdosing. Other compounds tested showed no significant analgesic effects on Taxol induced pain mice at 50 mg/kg via oral gavage feeding, although these data do not foreclose the demonstration of analgesic activity by this latter group of compounds, such as at different dosing or formulation, in different models or different organisms, or in actual human disease.

Figure 6:
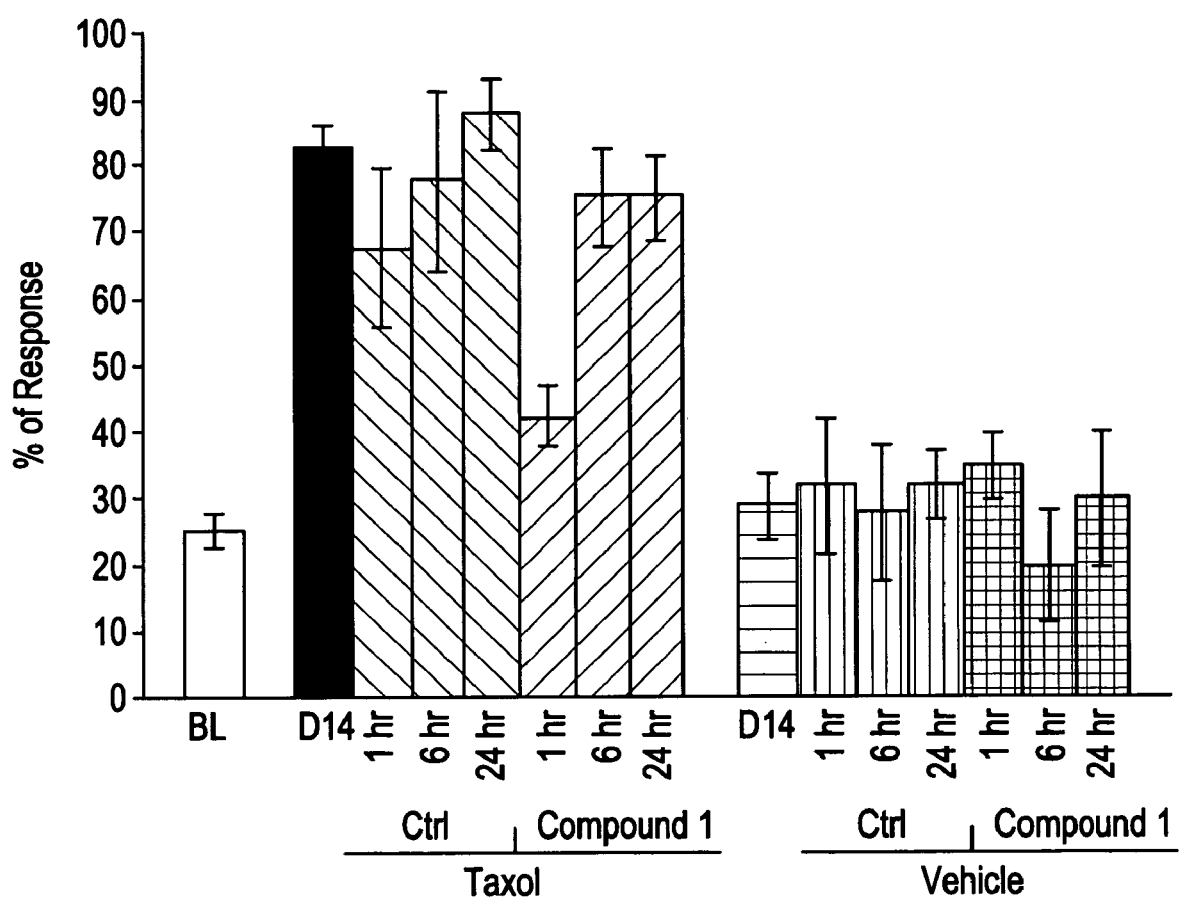
FIG. 6: A graph showing the analgesic effect of Compound 1 on mechanical allodynia of a taxol-induced neuropathic pain model.
Figure 7:
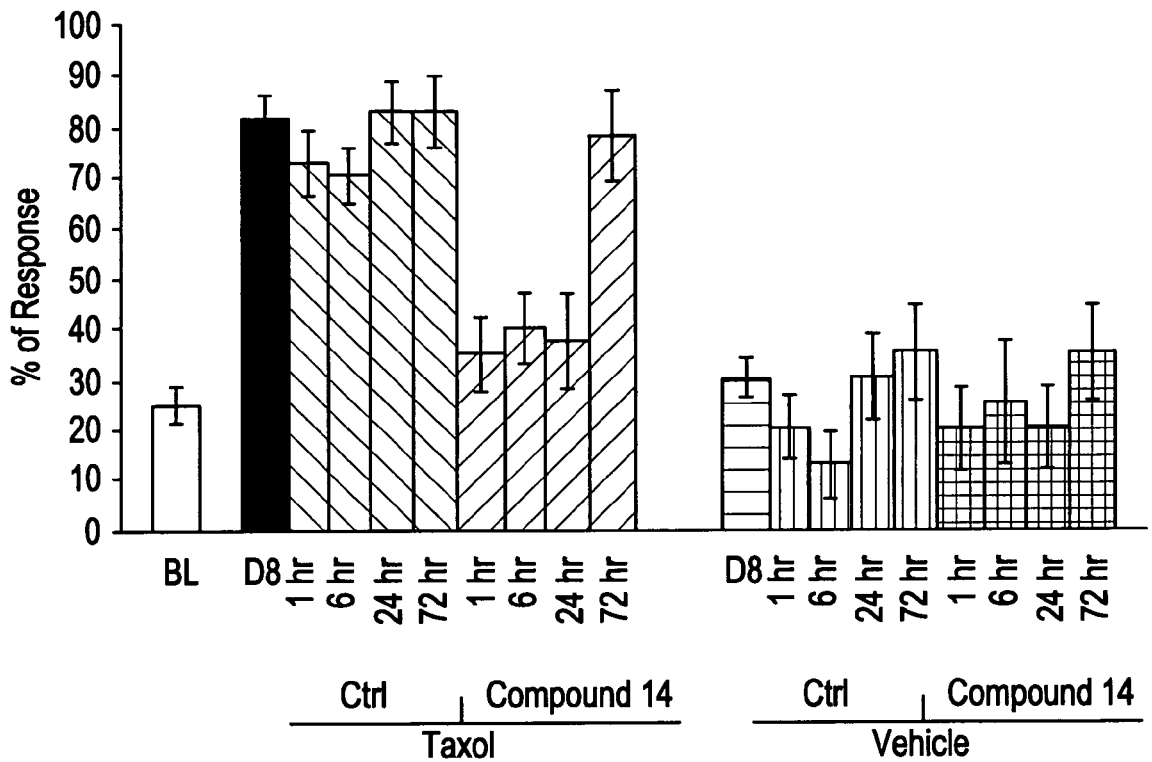
FIG. 7: A graph showing that Compound 14 inhibits mechanical allodynia in a taxol-induced neuropathic pain model.

The results demonstrating the effect of Compounds 1 and 14 are set forth in FIGS. 6 and 7, and a summary of results of all compounds is presented in the first eight rows of Table III, below. The last two rows in the table present the results of the testing of Compounds 1 and 14 in the Chung model, described in Example VI, below.

TABLE III

| Compound | Model/ species | Administration | Dosing | Mg/Kg body weight | Effective time Hour post dosing |
|---|---|---|---|---|---|
| Compound 1 | Taxol/mice | P.O. | Single | 50 | ~1, partial block |
| Compound 14 | Taxol/mice | P.O. | Single | 50 | ~24, block |
| Compound 16 | Taxol/mice | P.O. | Single | 50 | None via p.o. |
| Compound 4 | Taxol/mice | P.O. | Single | 50 | None via p.o. |
| Compound 7 | Taxol/mice | P.O. | Single | 50 | None via p.o. |
| Compound 6 | Taxol/mice | P.O. | Single | 50 | None via p.o. |
| Compound 15 | Taxol/mice | P.O. | Single | 50 | None via p.o. |
| Compound 21 | Taxol/mice | P.O. | Single | 50 | None via p.o. |
| Compound 14 | Spinal nerve ligation/rats | i.p. | Single | 25 | Analgesic up to 24 hour postdosing |
| Compound 23 | Spinal nerve ligation/rats | i.p. | Single | 25 | Analgesic up to 24 hour postdosing |

Example VI a. Neuropathic Pain Testing in a Spinal Nerve Ligation (Chung) Model

180–200 grams of body weight, male, Sprague-Dawley rats from Harlan were used. They were housed under the standard housing conditions and trained for 1 week before measurement of the baseline. The rats were prepared in the manner described in Example V, above, by i.p. admininstration of Taxol. The spinal nerve ligation surgery was performed as described by Kim & Chung (Kim, S. O., and Chung, J. M., An experimental model for peripheral neuropathy produced by segmental spinal nerve ligation in rat. Pain. 1992; 50:355–363.).

Figure 8:
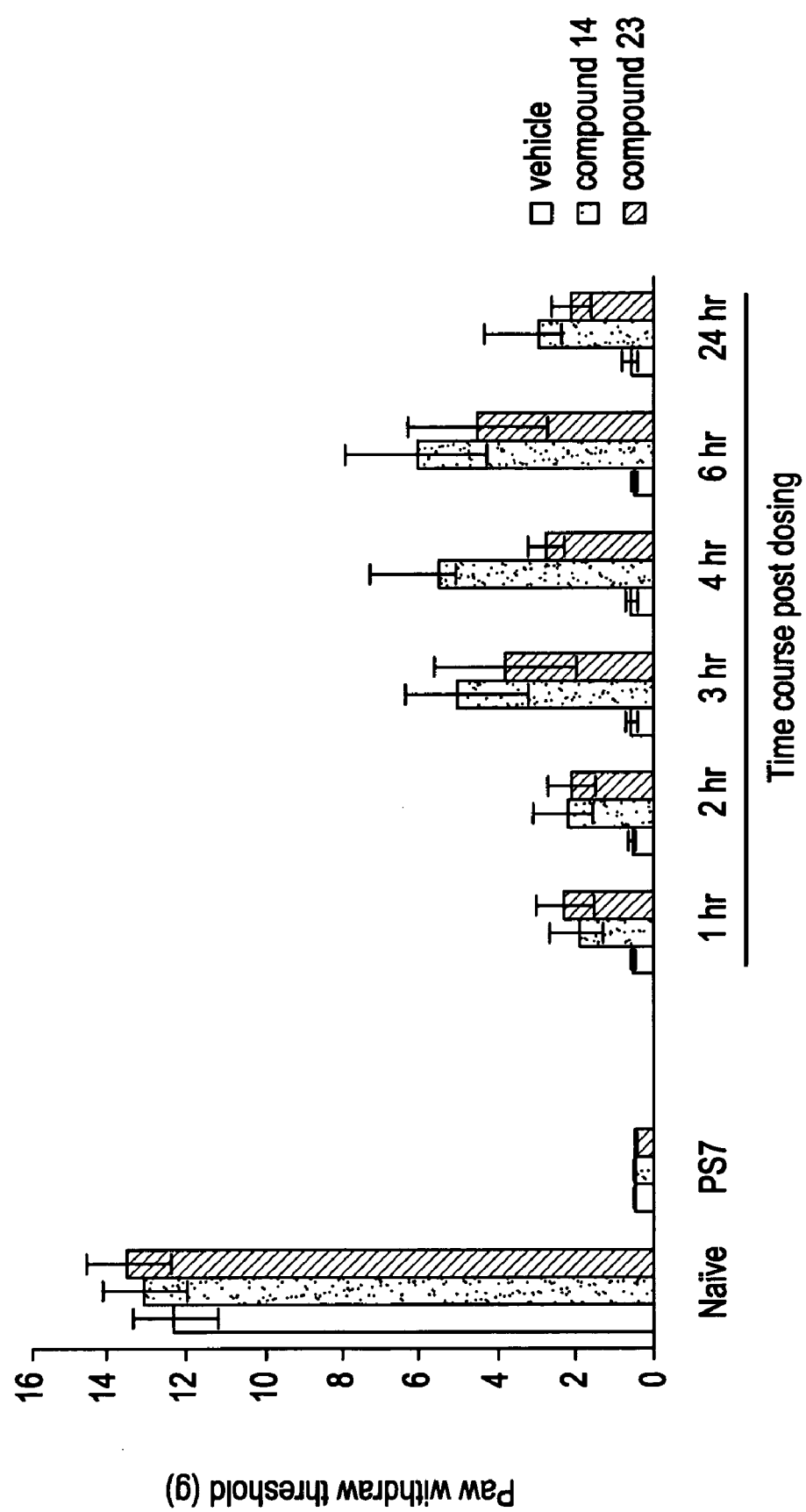
FIG. 8: A graph showing that Compounds 14 and 23 attenuate mechanical allodynia in a Chung model.

The development of neuropathic pain was measured using 50% of threshold measurement using von Frey filaments. Only those rats that exhibited a paw withdrawal threshold no greater than 7 grams for two consecutive day measurements were included for drug testing. Generally speaking, the mechanical allodynia in spinal nerve ligation model rats fell in the range of 1–4 grams of the paw withdrawal threshold. The results of the tests are set forth in FIG. 8 and are summarized in the last two rows of Table III.

b. Results

Two compounds, Compound 14 and Compound 23 were tested in the Chung model in rats at 25 mg/kg single dosing via i.p administration. Both compound showed significant analgesic effects over control, and maintained such effects over an extended period for one dose of the compound. These results further cooroborate the therapeutic activity of the compounds of the invention, and the corresponding pharmaceutical compositions that are taught herein.

From the foregoing description, various modifications and changes in the compositions and methods of this invention will occur to those skilled in the art. All such modifications coming within the scope of the appended claims are intended to be included therein.

What is claimed is:

1. A compound of formula 1

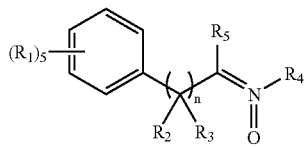

I wherein:
(i) n is an integer with a value ranging from two to six;
(ii) each $R_1$ is independently selected from:
hydrogen,
alkyl, alkenyl, alkynyl. cycloalkyl, cycloalkenyl, aryl, alkaryl, aralkyl, aralkenyl, aralkynyl,
halo, haloalkyl,
hydroxyl, alkoxyl, hydroxyalkyl, alkoxyalkoxyl, acyl, carboxylate, carboxyl, alkanoyloxy,
nitrate, nitrite, nitrile, cyanate, isocyanate, primary amino, secondary amino, tertiary amino, azido, carboxamido, acylamino,
thiol, sulfonyl, alkyl sulfonate, aryl sulfonate, sulfonamide, thioaryloxy, thioalkoxy,
oxygen heterocycles, nitogen heterocycles and sulfur heterocycles;

(iii) $R_2$, $R_3$ and $R_5$ are each independently selected from hydrogen, alkyl and cycloalkyl; and
(iv) $R_4$ is selected from alkyl, cycloalkyl, cycloalkylalkylene, cycloalkenyl, aryl and aralkyl,
provided that:
not all $R_1$s are hydrogen.

2. The compound of claim 1 wherein the $R_1$ groups include hydrogens and from one up to three nonhydrogens selected from alkyl, alkoxy, alkoxyalkoxyl, hydroxy, amino, dialkylamino, acylamino, sulfonyl, sulfonate, sulfonamide, acyl, and aryl.

3. The compound of claim 2 wherein n=2 and $R_2$, $R_3$ and $R_5$ are all hydrogens or up to two alkyls.

4. The compound of claim 1 wherein $R_1$ includes 1–5 halogens.

5. The compound of claim 1 wherein n is an integer having a value of from 2 through 4.

6. The compound of claim 1 wherein n=2 and $R_2$, $R_3$ and $R_5$ are all hydrogens and up to two lower alkyls.

7. The compound of claim 6 wherein $R_1$ and $R_4$ are selected from the group consisting of:

| $R_1$ | $R_4$ |
|---|---|
| H | $C(CH_3)_3$ |
| 4-Me | $C(CH_3)_3$ |
| 4-iso-Pr | $C(CH_3)_3$ |
| 4-OH | $C(CH_3)_3$ |
| 4-OMe | $C(CH_3)_3$ |
| 4-OCH$_2$OMe | $C(CH_3)_3$ |
| 4-OEt | $C(CH_3)_3$ |
| 4-NMe$_2$ | $C(CH_3)_3$ |
| 4-NHAc | $C(CH_3)_3$ |
| 4-F | $C(CH_3)_3$ |
| 4-Cl | $C(CH_3)_3$ |
| 2-SO$_3$Na | $C(CH_3)_3$ |
| 2,4-di-SO$_3$Na | $C(CH_3)_3$ |
| 3,5-di-t-Bu-4-OH | $C(CH_3)_3$ |
| 3,5-di-t-Bu-4-OCH$_2$OMe | $C(CH_3)_3$ |
| 2-OH | $C(CH_3)_3$ |
| 2-OEt | $C(CH_3)_3$ |

8. The compound of claim 1 selected from the group consisting of:

| | |
|---|---|
| Compound 2 | N-tert-butyl-C-{2-[4-(methoxymethoxy)phenyl]ethyl} nitrone |
| Compound 3 | N-tert-butyl-C-[2-(4-hydroxyphenyl)ethyl nitrone |
| Compound 4 | N-tert-butyl-C-[2-(4-methoxyphenyl)ethyl] nitrone |
| Compound 6 | N-tert-butyl-C-[2-(4-isopropoxyphenyl)ethyl] nitrone |
| Compound 7 | N-tert-butyl-C-[2-(4-ethoxyphenyl)ethyl] nitrone |
| Compound 8 | N-tert-butyl-C-[2-(4-benzenesulfonyloxy)phenyl]ethyl] nitrone |
| Compound 9 | N-tert-butyl-C-[2-(4-acetamidophenyl)ethyl] nitrone |
| Compound 10 | N-tert-butyl-C-[2-(4-benzenesulfonamidophenyl)ethyl] nitrone |
| Compound 11 | N-tert-butyl-C-[2-(4-N,N-Dibenzenesulfimidophenyl)ethyl] nitrone |
| Compound 13 | N-tert-butyl-C-[2-(4-isopropylphenyl)-1-methyethyl] nitrone |
| Compound 15 | N-tert-butyl-C-[1-(4-tert-butyl benzyl)-ethyl] nitrone |
| Compound 16 | N-tert-butyl-C-[1-methyl-2-(4-methoxyphenyl)ethyl] nitrone |
| Compound 21 | N-tert-butyl-C-[2-(3,5-di-tert-butyl-4-hydroxyphenyl)ethyl] nitrone |
| Compound 23 | N-tert-butyl-C-[4-methoxy-phenyl)propyl] nitrone, and pharmaceutically acceptable salts thereof. |

9. A nitrone compound having at least a Ph-Z-C(H)=N(=O)—$R^4$ where Ph represents a substituted aryl moiety, Z is a saturated aliphatic carbon chain of two to six carbon atoms in length, and $R^4$ is selected from alkyl, cycloalkyl, cycloalkylalkylene, cycloalkenyl, and aralkyl.

10. The nitrone compound of claim 9 wherein Z is a straight chain alkylene of two to six carbon length.

11. The nitrone compound of claim 10 wherein Z is ethylene.

12. The nitrone compound of claim 10 wherein Z is n-propylene.

13. The nitrone compound of claim 10 wherein Z is n-butylene.

14. The nitrone compound of claim 10 wherein the aryl moiety is phenyl substituted with one or two sulfonyls.

15. The nitrone compound of claim 10 wherein the aryl moiety is phenyl substituted with one or two lower alkyls and one hydroxyl.

16. The nitrone compound of claim 10 wherein the aryl moiety is phenyl substituted with one or two alkoxyls.

17. The nitrone compound of claim 9 wherein Z is a branched chain alkylene of two to six carbon length.

18. The nitrone compound of claim 11 wherein Z is isopropylene.

19. The nitrone compound of claim 9 wherein $R^4$ is a lower alkyl.

20. The nitrone compound of claim 19 wherein the lower alkyl is methyl.

21. The nitrone compound of claim 19 wherein the lower alkyl is tert-butyl.

22. A pharmaceutical composition comprising a pharmaceutically acceptable carrier and one or more compounds of formula I as active ingredients.

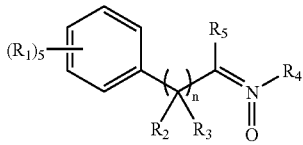

I wherein:

(i) n is an integer with a value ranging from two to six;

(ii) each $R_1$ is independently selected from:

hydrogen, alkyl, alkenyl, alkynyl. cycloalkyl, cycloalkenyl, aryl, alkaryl, aralkyl, aralkenyl, aralkynyl, halo, haloalkyl, hydroxyl, alkoxyl, hydroxyalkyl, alkoxyalkoxyl, acyl, carboxylate, carboxyl, alkanoyloxy, nitrate, nitrite, nitrite, cyanate, isocyanate, primary amino, secondary amino, tertiary amino, azido, carboxamido, acylamino, thiol, sulfonyl, alkyl sulfonate, aryl sulfonate, sulfonamide, thioaryloxy, thioalkoxy, oxygen heterocycles, nitrogen heterocycles and sulfur heterocycles;

(iii) $R_2$, $R_3$ and $R_5$ are each independently selected from hydrogen, alkyl and cycloalkyl; and (iv) $R_4$ is selected from alkyl, cycloalkyl, cycloalkylalkylene, cycloalkenyl, aryl and aralkyl provided that:

not all $R_1$s are hydrogen.

23. The composition of claim 22 wherein the $R_1$ groups include hydrogens and from zero up to three nonhydrogens selected from alkyl, alkoxy, alkoxyalkoxyl, halo, hydroxy, amino, dialkylamino, acylamino, sulfonyl, sulfonate, sulfonamide, acyl, and aryl.

24. The composition of claim 22 wherein n is an integer having a value of from 2 through 4.

25. The composition of claim 22 wherein n=2 and $R_2$, $R_3$ and $R_5$ are all hydrogens and up to two lower alkyls.

26. The composition of claim 25 wherein $R_1$ and $R_4$ are selected from the group consisting of:

| $R_1$ | $R_4$ |
|---|---|
| H | $C(CH_3)_3$ |
| 4-Me | $C(CH_3)_3$ |
| 4-iso-Pr | $C(CH_3)_3$ |
| 4-OH | $C(CH_3)_3$ |
| 4-OMe | $C(CH_3)_3$ |
| 4-OCH$_2$OMe | $C(CH_3)_3$ |
| 4-OEt | $C(CH_3)_3$ |
| 4-NMe$_2$ | $C(CH_3)_3$ |
| 4-NHAc | $C(CH_3)_3$ |
| 4-F | $C(CH_3)_3$ |
| 4-Cl | $C(CH_3)_3$ |
| 2-SO$_3$Na | $C(CH_3)_3$ |
| 2,4-di-SO$_3$Na | $C(CH_3)_3$ |
| 3,5-di-t-Bu-4-OH | $C(CH_3)_3$ |
| 3,5-di-t-Bu-4-OCH$_2$OMe | $C(CH_3)_3$ |
| 2-OH | $C(CH_3)_3$ |
| 2-OEt | $C(CH_3)_3$ |

27. The composition of claim 22 wherein n=2 and $R_2$, $R_3$ and $R_5$ are all hydrogens and up to two lower alkyls.

28. A pharmaceutical composition comprising a pharmaceutically-acceptable carrier and as active ingredients one or more compounds selected from the group consisting of:

| | |
|---|---|
| Compound 1 | N-tert-butyl-C-(2-phenylethyl) nitrone |
| Compound 2 | N-tert-butyl-C-{2-[4-(methoxymethoxy)phenyl]ethyl} nitrone |
| Compound 3 | N-tert-butyl-C-[2-(4-hydroxyphenyl)ethyl nitrone |
| Compound 4 | N-tert-butyl-C-[2-(4-methoxyphenyl)ethyl] nitrone |
| Compound 6 | N-tert-butyl-C-[2-(4-isopropoxyphenyl)ethyl] nitrone |
| Compound 7 | N-tert-butyl-C-[2-(4-ethoxyphenyl)ethyl] nitrone |
| Compound 8 | N-tert-butyl-C-[2-(4-benzenesulfonyloxy)phenyl]ethyl] nitrone |
| Compound 9 | N-tert-butyl-C-[2-(4-acetamidophenyl)ethyl] nitrone |
| Compound 10 | N-tert-butyl-C-[2-(4-benzenesulfonamidophenyl)ethyl] nitrone |
| Compound 11 | N-tert-butyl-C-[2-(4-N,N Dibenzenesulfimidophenyl)ethyl] nitrone |
| Compound 13 | N-tert-butyl-C-[2-(4-isopropylphenyl)-1-methyethyl] nitrone |
| Compound 15 | N-tert-butyl-C-[1-(4-tert-butyl benzyl)-ethyl] nitrone |
| Compound 16 | N-tert-butyl-C-[1-methyl-2-(4-methoxyphenyl)ethyl] nitrone |
| Compound 17 | N-tert-butyl-C phenylmethyl nitrone |
| Compound 20 | N-tert-butyl-C-[1-(phenyl)ethyl] nitrone |
| Compound 21 | N-tert-butyl-C-[2-(3,5-di-tert-butyl-4-hydroxyphenyl)ethyl] nitrone |
| Compound 23 | N-tert-butyl-C-[4-methoxy-phenyl)propyl] nitrone, and pharmaceutically acceptable salts thereof. |

29. A pharmaceutical composition comprising a pharmaceutical carrier and, as an active ingredient at least one nitrone compound, the nitrone compound having a formula Ph-Z-C(H)=N(=O)—R$^4$ where Ph represents a substituted aryl moiety, and Z is a saturated aliphatic carbon chain of two to six carbon atoms in length, and R$^4$ is selected from alkyl, cycloalkyl, cycloalkylalkylene, cycloalkenyl, and aralky.

30. The pharmaceutical composition of claim 29 wherein Z is a straight chain alkylene of two to six carbon atoms in length.

31. The pharmaceutical composition of claim 30 wherein Z is ethylene.

32. The pharmaceutical composition of claim 30 wherein Z is n-propylene.

33. The pharmaceutical composition of claim 30 wherein Z is n-butylene.

34. The pharmaceutical composition of claim 30 wherein Z is isopropylene.

35. The pharmaceutical composition of claim 29 wherein Z is a branched chain alkylene of two to six carbon atoms in length.

36. The pharmaceutical composition of any of claims 22–34 wherein the carrier is an injectable carrier.

37. The pharmaceutical composition of any of claims 22–34 wherein the composition is a solid carrier.

38. The pharmaceutical composition of any of claims 22–34 wherein the composition is a unit dose form.

39. A method for treating or preventing inflammation in a mammal comprising administering said mammal an effective inflammation treating or preventing dose of a pharmaceutical composition according to any of claims 22–38.

40. A method for treating or preventing neuropathic pain in a mammal comprising administering said mammal an effective neuropathic pain treating or preventing dose of a pharmaceutical composition according to any of claims 22–38.

41. A method for the treatment of traumatic injury to the brain or spinal cord of a mammal comprising administering said mammal an effective brain or spinal cord injury treating dose of a pharmaceutical composition according to any of claims 22–38.

42. The method of any of claims 39–41 wherein the mammal is a human.

43. A pharmaceutical composition for treating inflammation, neuropathic pain, neurodegenerative disease, pain associated with arthritis or traumatic injury to the brain or spinal cord of a mammal comprising a pharmaceutically acceptable carrier and one or more compounds of formula I as active ingredients

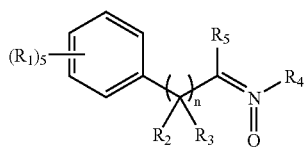

I wherein:
(i) n is an integer with a value ranging from one to six;
(ii) each R$_1$ is independently selected from:
   hydrogen,
   alkyl, alkenyl, alkynyl. cycloalkyl, cycloalkenyl, aryl, alkaryl, aralkyl, aralkenyl, aralkynyl,
   halo, haloalkyl,
   hydroxyl, alkoxyl, hydroxyalkyl, alkoxyalkoxyl, acyl, carboxylate, carboxyl, alkanoyloxy,
   nitrate, nitrite, nitrile, cyanate, isocyanate, primary amino, secondary amino, tertiary amino, azido, carboxamido, acylamino,
   thiol, sulfonyl, alkyl sulfonate, aryl sulfonate, sulfonamide, thioaryloxy, thioalkoxy,
   oxygen heterocycles, nitogen heterocycles and sulfur heterocycles;
(iii) R$_2$, R$_3$ and R$_5$ are each independently selected from hydrogen, alkyl and cycloalkyl; and
(iv) R$_4$ is selected from alkyl, cycloalkyl, cycloalkylalkylene, cycloalkenyl, aryl and aralkyl.

44. The composition of claim 43 wherein the R$_1$ groups include hydrogens and from zero up to three nonhydrogens selected from alkyl, alkoxy, alkoxyalkoxyl, halo, hydroxy, amino, dialkylamnmo, acylamino, sulfonyl, sulfonate, sulfbnamide, acyl, and aryl.

45. The composition of claim 44 wherein R$_1$, and R$_4$ are selected from the group consisting of:

TABLE II

| R$_1$ | R$_4$ |
|---|---|
| H | C(CH$_3$)$_3$ |
| 4-Me | C(CH$_3$)$_3$ |
| 4-iso-Pr | C(CH$_3$)$_3$ |
| 4-OH | C(CH$_3$)$_3$ |
| 4-OMe | C(CH$_3$)$_3$ |
| 4-OCH$_2$OMe | C(CH$_3$)$_3$ |
| 4-OEt | C(CH$_3$)$_3$ |
| 4-NMe$_2$ | C(CH$_3$)$_3$ |
| 4-NHAc | C(CH$_3$)$_3$ |
| 4-F | C(CH$_3$)$_3$ |
| 4-Cl | C(CH$_3$)$_3$ |
| 2-SO$_3$Na | C(CH$_3$)$_3$ |
| 2,4-di-SO$_3$Na | C(CH$_3$)$_3$ |
| 3,5-di-t-Bu-4-OH | C(CH$_3$)$_3$ |
| 3,5-di-t-Bu-4-OCH$_2$OMe | C(CH$_3$)$_3$ |
| 2-OH | C(CH$_3$)$_3$ |
| 2-OEt | C(CH$_3$)$_3$ |

46. The composition of claim 43 wherein n is an integer having a value of from 1 through 4.

47. The composition of claim 43 wherein n=1 and R$_2$, R$_3$ and R$_5$ are together all hydrogen or two hydrogen and one lower alkyl; and materials in which n=2 or 3 and R$_2$, R$_3$ and R$_5$ are all hydrogens and up to two lower alkyls.

48. The composition of claim 43 wherein n=1 and R$_2$, R$_3$ and R$_5$ and together all hydrogen or two hydrogens and one lower alkyl; and materials in which n=2 or 3 and R$_2$, R$_3$ and R$_5$ are all hydrogens and up to two lower alkyls.

49. A pharmaceutical composition comprising a pharmaceutically-acceptable carrier and as active ingredients one or more compounds selected from the group consisting of:

| | |
|---|---|
| Compound 1 | N-tert-butyl-C-(2-phenylethyl) nitrone |
| Compound 2 | N-tert-butyl-C-{2-[4-(methoxymethoxy)phenyl]ethyl} nitrone |
| Compound 3 | N-tert-butyl-C-[2-(4-hydroxyphenyl]ethyl nitrone |

-continued

| | |
|---|---|
| Compound 4 | N-tert-butyl-C-[2-(4-methoxyphenyl)ethyl] nitrone |
| Compound 5 | N-tert-butyl-C-[4-(tetrahydropyran-2-yloxy) phenyl] nitrone |
| Compound 6 | N-tert-butyl-C-[2-(4-isopropoxyphenyl)ethyl] nitrone |
| Compound 7 | N-tert-butyl-C-[2-(4-ethoxyphenyl)ethyl] nitrone |
| Compound 8 | N-tert-butyl-C-[2-(4-benzenesulfonyloxy)phenyl]ethyl] nitrone |
| Compound 9 | N-tert-butyl-C-[2-(4-acetamidophenyl)ethyl] nitrone |
| Compound 10 | N-tert-butyl-C-[2-(4-benzenesulfonamidophenyl)ethyl] nitrone |
| Compound 11 | N-tert-butyl-C-[2-(4-N,N-Dibenzenesulfimidophenyl)ethyl] nitrone |
| Compound 12 | N-tert-butyl-C-(5-phenylpentyl) nitrone |
| Compound 13 | N-tert-butyl-C-[2-(4-isopropylphenyl)-1-methyethyl] nitrone |
| Compound 14 | N-tert-butyl-C-(4-phenylpropyl) nitrone |
| Compound 15 | N-tert-butyl-C-[1-(4-tert-butyl benzyl)-ethyl] nitrone |
| Compound 16 | N-tert-butyl-C-[1-methyl-2-(4-methoxyphenyl)ethyl] nitrone |
| Compound 17 | N-tert-butyl-C phenylmethyl nitrone |
| Compound 18 | N-cyclohexyl-C-(2-phenylethyl) nitrone |
| Compound 19 | N-tert-butyl-C-[4-phenylbutyl] nitrone |
| Compound 20 | N-tert-butyl-C-[1-(phenyl)ethyl] nitrone |
| Compound 21 | N-tert-butyl-C-[2-(3,5-di-tert-butyl-4-hydroxyphenyl)ethyl] nitrone |
| Compound 22 | N-tert-butyl-C-[2-(3,5-di-tert-butyl-4-hydroxyphenyl)methyl] nitrone |
| Compound 23 | N-tert-butyl-C-[4-methoxy-phenyl)propyl] nitrone, and pharmaceutically acceptable salts thereof. |

50. A pharmaceutical composition conprising a pharmaceutical carrier and, as are active ingredient at least one nitrone compound, the nitrone compound comprising at least a Ph-Z-C(H)=N(=O)— where Ph represents a substituted or unsubstituted aryl moiety, and Z is a saturated aliphatic carbon chain of one to six carbon atoms in length covalently bonded intermediate the aryl moiety and the nitrone carbon.

51. The pharmaceutical composition of claim 50 wherein Z is a straight chain alkylene.

52. The pharmaceutical composition of claim 50 wherein Z is a branched chain alkylene.

53. The pharmaceutical composition of claim 50 wherein Z is methylene.

54. The pharmaceutical composition of claim 50 wherein Z is ethylene.

55. The pharmaceutical composition of claim 50 wherein Z is n-propylene.

56. The pharmaceutical composition of claim 50 wherein Z is n-butylene.

57. The pharmaceutical composition of claim 50 wherein Z is isopropylene.

58. The pharmaceutical composition of amy of claims 43–57 wherein the carrier is an injectable carrier.

59. The pharmaceutical composition of any of claims 43–57 wherein the composition is a solid carrier.

60. The pharmaceutical composition of any of claims 43–57 wherein the composition is a unit dose form.

61. The pharmaceutical composition of any of claims 43–57 wherein the inflammation is associated with rheumatoid arthritis, osteoarthritis, ankylosing spondylitis, systemic lupus erythematosus, psoriatic arthritis or neurodegenerative disease.

62. The pharmaceutical composition of any of claims 43–57 wherein the neurodegenerative disease is selected from the group consisting of Alzheimer's Disease, Parkinson's Disease, and Amyotrophic Lateral Sclerosis.

* * * * *